US007449562B2

(12) United States Patent  (10) Patent No.: US 7,449,562 B2
Herring et al.  (45) Date of Patent: Nov. 11, 2008

(54) PERV SCREENING METHOD AND USE THEREOF

(75) Inventors: Christopher Herring, Abington (GB); Gillian Langford, London (GB); Gary Quinn, Melrose, MA (US); Linda Scobie, Glasgow (GB)

(73) Assignee: Novartis AG, Basel (CH)

( * ) Notice: Subject to any disclaimer, the term of this patent is extended or adjusted under 35 U.S.C. 154(b) by 240 days.

(21) Appl. No.: 10/481,160

(22) PCT Filed: Jun. 28, 2002

(86) PCT No.: PCT/EP02/07159

§ 371 (c)(1), (2), (4) Date: Sep. 14, 2004

(87) PCT Pub. No.: WO03/002746

PCT Pub. Date: Jan. 9, 2003

(65) Prior Publication Data

US 2005/0066380 A1  Mar. 24, 2005

Related U.S. Application Data

(60) Provisional application No. 60/302,133, filed on Jun. 29, 2001.

(51) Int. Cl.
C07H 21/04 (2006.01)
C12P 19/34 (2006.01)
(52) U.S. Cl. .......... 536/23.1; 536/24.3; 536/24.32; 435/6; 435/91.2
(58) Field of Classification Search .......... None
See application file for complete search history.

(56) References Cited

U.S. PATENT DOCUMENTS

| 4,980,286 | A | 12/1990 | Morgan et al. ........... 435/172.3 |
|---|---|---|---|
| 5,166,320 | A | 11/1992 | Wu et al. ................... 530/395 |
| 5,173,414 | A | 12/1992 | Lebkowski et al. ....... 435/172.3 |
| 5,219,740 | A | 6/1993 | Miller et al. ............... 435/69.6 |
| 5,252,479 | A | 10/1993 | Srivastava ................ 435/235.1 |
| 5,413,923 | A | 5/1995 | Kucherlapati et al. ..... 435/172.3 |
| 5,416,260 | A | 5/1995 | Koller et al. .................... 800/2 |
| 5,552,311 | A | 9/1996 | Sorscher et al. .......... 435/240.2 |
| 5,574,205 | A | 11/1996 | Kucherlapati et al. .......... 800/2 |
| 5,604,090 | A | 2/1997 | Alexander et al. ............. 435/5 |
| 5,658,785 | A | 8/1997 | Johnson ...................... 435/367 |
| 5,728,399 | A | 3/1998 | Wu et al. .................... 424/450 |
| 5,763,416 | A | 6/1998 | Bonadio et al. ............... 514/44 |
| 5,773,289 | A | 6/1998 | Samulski et al. ......... 435/320.1 |
| 5,824,544 | A | 10/1998 | Armentano et al. ....... 435/320.1 |
| 5,834,182 | A | 11/1998 | Alexander et al. ............. 435/5 |
| 5,843,742 | A | 12/1998 | Natsoulis et al. ......... 435/172.3 |
| 5,868,040 | A | 2/1999 | Papenhagen et al. .......... 74/513 |
| 5,869,040 | A | 2/1999 | Oin .......................... 424/93.21 |
| 5,871,722 | A | 2/1999 | Nacht et al. .............. 424/78.03 |
| 5,874,297 | A | 2/1999 | Wu et al. ................... 435/320.1 |
| 5,880,102 | A | 3/1999 | George et al. ................. 514/44 |
| 5,882,877 | A | 3/1999 | Gregory et al. .......... 435/320.1 |
| 5,885,808 | A | 3/1999 | Spooner et al. .......... 435/172.3 |
| 5,932,210 | A | 8/1999 | Gregory et al. ........... 424/93.2 |
| 5,942,496 | A | 8/1999 | Bonadio et al. ............... 514/44 |
| 5,948,675 | A | 9/1999 | Klatzmann et al. ....... 435/320.1 |
| 5,981,225 | A | 11/1999 | Kochanek et al. .......... 435/69.1 |
| 5,994,106 | A | 11/1999 | Kovesdi et al. ............. 435/91.4 |
| 5,994,132 | A | 11/1999 | Chamberlain et al. ....... 435/369 |
| 6,001,557 | A | 12/1999 | Wilson et al. .................. 435/5 |
| 6,030,954 | A | 2/2000 | Wu et al. ....................... 514/44 |
| 6,033,884 | A | 3/2000 | Woo et al. ................. 435/172.3 |
| 6,190,861 | B1 * | 2/2001 | Fishman ......................... 435/5 |
| 7,038,107 | B2 * | 5/2006 | Cui et al. ...................... 800/17 |

FOREIGN PATENT DOCUMENTS

| WO | WO 92/06180 | 4/1992 |
|---|---|---|
| WO | WO 92/20316 | 11/1992 |
| WO | WO 92/22635 | 12/1992 |
| WO | WO 93/14188 | 7/1993 |
| WO | WO 93/20221 | 10/1993 |
| WO | WO 94/08598 | 4/1994 |
| WO | WO 9853104 A2 * | 11/1998 |
| WO | WO 00/71726 | 11/2000 |
| WO | WO 0071726 A1 * | 11/2000 |
| WO | WO 02/072836 | 9/2002 |

OTHER PUBLICATIONS

Czauderna et al. J Virol 2000;74:4028-38.*
Akiyoshi et al., "Identification of a Full-Length cDNA for an Endogenous Retrovirus of Miniature Swine", *J Virol*, vol. 72, No. 5, pp. 4503-4507 (1998).
*Animal Cell Culture: A Practical Approach*, Second Edition, Freshney, Ed., IRL Press, Oxford University Press (1986).
*Antibodies: A Laboratory Manual*, Harlow and Lane, Eds., Cold Spring Harbor Press, NY (1988).
*A Practical Guide to Molecular Cloning*, Perbal, Ed., John Wiley & Sons, NY (1984).
Ausubel et al., "Preparing Lambda DNA from Phage Lysates", *Curr Prot Mol Biol*, vol. 1, Unit 1.13, Suppl. 10, pp. 1.13.1-1.13.10 (1990).
Blusch et al., "Infection of Nonhuman Primate Cells by Pig Endogenous Retrovirus", *J Virol*, vol. 74, No. 16, pp. 7687-7690 (2000).
Bösch, Arnauld and Jestin, "Study of Full-Length Porcine Endogenous Retrovirus Genomes with Envelope Gene Polymorphism in a Specific-Pathogen-Free Large White Swine Herd", *J Virol*, vol. 74, No. 18, pp. 8575-8581 (2000).
Chee et al., "Accessing Genetic Information with High-Density DNA Arrays", *Science*, vol. 274, No. 5287, pp. 610-614 (1996).
Colowick and Kaplan, "*Methods in Enzymology*, vol. 135: Immobilized Enzymes and Cells. Part B", Mosbach, Ed., Academic Press, Inc. (1987).

(Continued)

*Primary Examiner*—Q. Janice Li
(74) *Attorney, Agent, or Firm*—Choate, Hall & Stewart LLP

(57) ABSTRACT

The invention relates to porcine endogenous retrovirus (PERV) and novel methods of identification, isolation and screening via polynucleotide sequences. It also relates to use of said methods in providing a pig that does not express porcine endogenous retrovirus. The organs, tissues and cells of said pig being capable of use for xenotransplantaion.

9 Claims, No Drawings

OTHER PUBLICATIONS

Colowick and Kaplan, *Methods in Enzymology*, vol. 155: Recombinant DNA, Part F", Wu, Ed., Academic Press, Inc. (1987).

Cotton, Rodrigues and Campbell, "Reactivity of Cytosine and Thymine in Single-Base-Pair Mismatches with Hydroxylamine and Osmium Tetroxide and Its Application to the Study of Mutations", *Proc Natl Acad Sci USA*, vol. 85, pp. 4397-4401 (1988).

Cozzi et al., Long-Term Survival of Nonhuman Primates Receiving Life-Supporting Transgenic Porcine Kidney Xenografts, *Transplantation*, vol. 70, No. 1, pp. 15-21 (2000).

Czauderna et al., "Establishment and Characterization of Molecular Clones of Porcine Endogenous Retroviruses Replicating on Human Cells", *J Virol*, vol. 74, No. 9, pp. 4028-4038 (2000).

Deng et al., "Mapping Dispersed Repetitive Loci Using Semi-Specific PCR Cloning and Somatic Cell Hybrid Mapping", *Nucleic Acids Res*, vol. 28, No. 23, e103, pp. 1-4 (2000).

Dexter, Allen and Lajtha, "Conditions Controlling the Proliferation of Haemopoietic Stem Cells in Vitro", *J Cell Physiol*, vol. 91, No. 3, pp. 335-344 (1976).

*DNA Cloning: A Practical Approach*, vols. I and II, Glover, Ed., IRL Press (1985).

*Gene Transfer Vectors for Mammalian Cells*, Miller and Calos, Eds., Current Communications in Molecular Biology (1987).

Heneine et al., "No Evidence of Infection with Porcine Endogenous Retrovirus in Recipients of Porcine Islet-Cell Xenograf", *Lancet*, vol. 352, No. 9129, pp. 695-699 (1998).

Herring et al., "Monitoring Xenotransplant Recipients for Infection by PERV", *Clin Biochem*, vol. 34, No. 1, pp. 23-27 (2001).

Herring et al., "Mapping Full-Length Porcine Endogenous Retroviruses in a Large White Pig", *J Virol*, vol. 75, No. 24, pp. 12252-12265 (2001).

Hug et al., "Analysis of Mice Containing a Targeted Deletion of Beta-Globin Locus Control Region 5' Hypersensitive Site 3", *Mol Cell Biol*, vol. 16, No. 6, pp. 2906-2912 (1996).

*Introduction to Computational Biology: Maps, Sequences and Genomes*, Chapman & Hall, Eds., London (1994).

Jin et al., "Expression of Porcine Endogenous Retrovirus in Peripheral Blood Leukocytes from Ten Different Breeds", *Transpl Infect Dis*, vol. 2, No. 1, pp. 11-14 (2000).

Kodo, Gale and Saxon, "Antibody Synthesis by Bone Marrow Cells In Vitro Following Primary and Booster Tetanus Toxoid Immunization in Humans", *J Clin Invest*, vol. 73, No. 5, pp. 1377-1384 (1984).

Levy et al., "Liver Allotransplantation after Extracorporeal Hepatic Support with Transgenic (hCD55/hCD59) Porcine Livers: Clinical Results and Lack of Pig-to-Human Transmission of the Porcine Endogenous Retrovirus", *Transplantation*, vol. 69, No. 2, pp. 272-280 (2000).

Martin et al., "Expression of Pig Endogenous Retrovirus by Primary Porcine Endothelial Cells and Infection of Human Cells", *Lancet*, vol. 352, No. 9129, pp. 692-694 (1998).

Martin et al., "Porcine Endogenous Retrovirus (PERV) was Not Transmitted from Transplanted Porcine Endothelial Cells to Baboons In Vivo", *Transpl Int*, vol. 11, No. 4, pp. 247-251 (1998).

Martin et al., "Productive Infection of Primary Human Endothelial Cells by Pig Endogenous Retrovirus (PERV)", *Xenotransplantation*, vol. 7, No. 2, pp. 138-142 (2000).

McCreath et al., "Production of Gene-Targeted Sheep by Nuclear Transfer from Cultured Somatic Cells", *Nature*, vol. 405, No. 6790, pp. 1066-1069 (1998).

*Molecular Cloning: A Laboratory Manual*, Second Edition, Sambrook, Fritsch and Maniatis, Eds., Cold Spring Harbor Press, NY (1989).

Myers, Larin and Maniatis, "Detection of Single Base Substitutions by Ribonuclease Cleavage at Mismatches in RNA:DNA Duplexes", *Science*, vol. 230, pp. 1242-1246 (1985).

*Nucleic Acid Hybridization*, Hames and Higgins, Eds., IRL Press (1985).

*Oligonucleotide Synthesis. A Practical Approach*, Gait, Ed., IRL Press (1984).

Paradis et al., "Search for Cross-Species Transmission of Porcine Endogenous Retrovirus in Patients Treated with Living Pig Tissue", *Science*, vol. 285, No. 5431, pp. 1236-1241 (1999).

Patience, Takeuchi and Weiss, "Infection of Human Cells by an Endogenous Retrovirus of Pigs", *Nat Med*, vol. 3, No. 3, pp. 282-286 (1997).

Patience et al., "No Evidence of Pig DNA or Retroviral Infection in Patients with Short-Term Extracorporeal Connection to Pig Kidneys", *Lancet*, vol. 352, No. 9129, pp. 699-701 (1998).

Pham et al., "Long-Range Disruption of Gene Expression by a Selectable Marker Cassette", *Proc Natl Acad Sci USA*, vol. 93, No. 23, pp. 13090-13095 (1996).

Pitkin and Mullon, "Evidence of Absence of Porcine Endogenous Retrovirus (PERV) Infection in Patients Treated with a Bioartificial Liver Support System", *Artif Organs*, vol. 23, No. 9, pp. 829-833 (1999).

Pittelkow and Scott, "New Techniques for the In Vitro Culture of Human Skin Keratinocytes and Perspectives on Their Use for Grafting of Patients with Extensive Burns", *Mayo Clin Proc*, vol. 61, pp. 771-777 (1986).

Powell et al., "Antiretroviral Agents Inhibit Infection of Human Cells by Porcine Endogenous Retroviruses", *Antimicrob Agents Chemther*, vol. 44, No. 12, pp. 3432-3433 (2000).

Rheinwald, "Chapter 15. Serial Cultivation of Normal Human Epidermal Keratinocytes", *Methods Cell Biol*, vol. 21A, pp. 229-254 (1980).

Roest et al., "Protein Truncation Test (PTT) for Rapid Detection of Translation-Terminating Mutations", *Hum Mol Genet*, vol. 2, No. 10, pp. 1719-1721 (1993).

Schmoeckel et al., "Orthotopic Heart Transplantation in a Transgenic Pig-to-Primate Model", *Transplantation*, vol. 65, No. 12, pp. 1570-1577 (1998).

Schumacher et al., "Transplantation of Embryonic Porcine Mesencephalic Tissue in Patients with PD", *Neurology*, vol. 54, No. 5, pp. 1042-1050 (2000).

Siebert et al., "An Improved PCR Method for Walking in Uncloned Genomic DNA", *Nucleic Acids Res*, vol. 23, No. 6, pp. 1087-1088 (1995).

Stemple and Anderson, "Isolation of a Stem Cell for Neurons and Glia from the Mammalian Neural Crest", *Cell*, vol. 71, No. 6, pp. 973-985 (1992).

Takeuchi et al., "Host Range and Interference Studies of Three Classes of Pig Endogenous Retrovirus", *J Virol*, vol. 72, No. 12, pp. 9986-9991 (1998).

Tönjes, Czauderna and Kurth, "Genome-Wide Screening, Cloning, Chromosomal Assignment, and Expression of Full-Length Human Endogenous Retrovirus Type K", *J Virol*, vol. 73, No. 11, pp. 9187-9195 (1999).

*Transcription and Translation. A Practical Approach*, Hames and Higgins, Eds., IRL Press (1985).

Waterworth et al., "Life-Supporting Pig-to-Baboon Heart Xenotransplantation", *J Heart Lung Transpl*, vol. 17, No. 12, pp. 1201-1207 (1998).

Whitlock and Witte, "Long-Term Culture of B Lymphocytes and Their Precursors from Murine Bone Marrow", *Proc Natl Acad Sci USA*, vol. 79, No. 11, pp. 3608-3612 (1982).

Wilson, Wong, VanBrocklin and Federspiel, "Extended Analysis of the In Vitro Tropism of Porcine Endogenous Retrovirus", *J Virol*, vol. 74, No. 1, pp. 49-56 (2000).

Wolf, Zakhartchenko and Brem, "Nuclear Transfer in Mammals: Recent Developments and Future Perspectives", *J Biotechnol*, vol. 65, pp. 99-110 (1998).

Zaidi et al., "Life-Supporting Pig-to-Primate Renal Xenotransplantation Using Genetically Modified Donors", *Transplantation*, vol. 65, No. 12, pp. 1584-1590 (1998).

Zijlstra et al., "Germ-Line Transmission of a Disrupted $\beta_2$-Microglobulin Gene Produced by Homologous Recombination in Embryonic Stem Cells", *Nature*, vol. 342, No. 6248, pp. 435-438 (1989).

* cited by examiner

SEQUENCE LISTING

<160> NUMBER OF SEQ ID NOS: 8

<210> SEQ ID NO 1
<211> LENGTH: 2860
<212> TYPE: DNA
<213> ORGANISM: Porcine endogenous retrovirus
<220> FEATURE:
<221> NAME/KEY: vector
<222> LOCATION: (1)..(21)
<220> FEATURE:
<221> NAME/KEY: primer
<222> LOCATION: (2536)..(2556)
<220> FEATURE:
<221> NAME/KEY: primer
<222> LOCATION: (2661)..(2678)
<220> FEATURE:
<221> NAME/KEY: LTR
<222> LOCATION: (2661)..(2860)
<220> FEATURE:
<221> NAME/KEY: primer
<222> LOCATION: (2839)..(2858)

<400> SEQUENCE: 1

```
gtaatacgac tcactatagg gcacgcgtgg tcgacggccc gggctggtct gctggcctaa      60
gccatagcca cagtaatgag ggatccaagc tgtgtctgtg acctacacca cagctcaggg     120
caacgccaga ttcttaaccc actgagtgag gccaggatc aaactcacaa cctcattgtt     180
cccagttgga ttcattctac tgcaccatga caggaactcc tatccagctc cttttgagtt     240
tctgtaaaag ttaaaattat ttttgtccta ggtctatgaa aatgccattg ataacttgat     300
agggattgaa ttgaatctgt agattgcctt ggatagtata atcatttga cagtattaag     360 gctttcagtc caagaacata gtatgtcttt ccatctcttt gtattatctt tgctttcttt     420
cataaatatt ttatactttt cagagtacta gattttgctt cctcaggaag gtttattcct     480 tggtattta ctcttttga tgtaatggta ataatattt tttctgtaat ttctatttct     540
gatctttcaa gtatatagaa gtataagata tttctgtgta ttaattttgt attctgcaac     600
tttaatgaat tcatttatga gaggtagtag ttttctggta gcatctttag gattgtctat     660
gtatagtatc atgtcatctg caaagaatta caatttatt tcttttccaa tttggattcc     720
ttttatcatt tcttctctg attaccatgg ctaggacttg caaaactgta ttgaataaaa     780
gtggtgagag tgggcatcca tgtcttgttc catatcttag agaaaacact ttcagctttt     840
cattgttgag tatattacct gtcagtttgt catatatggc ctttattatg ttgaggtagg     900
tgcgtccttg cccagtttct agagaatttt ttttaacat gaatgttgaa ctttattaaa     960 aacttttct acatctagtg agatgatcat atggttttaa ttattatc tgttaatgtg    1020 atgtatcaca ctgattaact cgtggatact gaaaaatcct tgcatccctg ggataaatcc    1080
tacttgatca tgtgtatgat ccttttaatg tattgttgga ttcagtttgc tggtattttg    1140
ttgaggattt ttgcattcat attaatagtg atattggcct gtaattttct ttttttgtggt    1200 attttttgta gttttttaata ccagggtgat ggtggtttca cagaatgcat ttggaagttt    1260
cccttccttg gcaattttt ggcatagttc cagaaggata gatattaact tttctctaaa    1320
tatctggtag aattcacctg tgaagtcatc tggtcctgga ctttgttgtg aactttttaa    1380
tcacagattt gatttcggta cttgaaattt gtctgctttt attttctatt ttttcctggt    1440
ttcgtcttta gagattatac tttgctaaaa atttgtccat ttattctgtg ttgtctatct    1500
tactggcata tagttgcttg cagtagtctt ttatggttct ccatattttc tgtagtgttg    1560
```

-continued

```
cttgtaactt ctgtttcatt taaatttaat tgatttaggc tctctccttt tttgcttgat    1620
gagtctagct aaagatttgt caatgttgtt cacagtacca ggttttagtt ttactaaaaa    1680
cctatagaaa ggatcaataa gtctctaatt catttatttc ttctctgatc tttatgattt    1740
cttctactaa ctgggttttt ttgttgttgt tgtcattgtt cttcttaggt tgcattaagt    1800
gtaaaggtag gttgtttatt tgtgattttt cttgtttgct gaggtaaata cgtattgtta    1860
taaacactcc tcttagaact gttttgctg agtcctgtag ctttggatc atcacatttt      1920
tgttttcatt tgtcactatt taatttgtat ttttacttc ctcttggatt tcttcagtga     1980
tccattgatt gtttgtagca gatcatctag cctccacatg tttgtgtttt tttgcaattt    2040
ttttcttgta gttgactgct aatttcatag cattgtggtc agaaaagatg cttggcatga    2100
tttcaattgt tttttctct tttggctatc ctttaatcta aggagttcct cacttccaga     2160
cccttatccc actgtgctgg gctggattcc agcactccaa agacactgac aatgcctttg    2220
caccaccaca ggaaatcctg atttcaattt tcttatattt accaagaatt gctttctagc    2280
actacatgtg ccagatctag tctggagaat gtgccatgtg cacttgaaaa gagggtgtat    2340
tctgatgctt tgaatggatt tttttaagta aataacaaat caatctagtc taatgtgtca    2400
tttaaatatt gtgttttctt attgactttg tctatctatc cattgctata agtggggtat    2460
taaagttaca cactattatt gttagagtca atttcaccta ttatggcttt taacatttgc    2520
cttacatgtt gaggtgatcc tatgttgggt gcatttttat ttcaaattgt taaatcttgg    2580
attgagccct tgatcatgat gtagtgccct tcttttctc ttgtaacagt ctttatttc      2640
gtgtctattt tgtctgatag tgaaaggcca gtaaagaac aatcccctc gtccgggctc      2700
ggaagaggcg acaccccaaa tcactcacga gaagcggtct tgatgcaaac agcaagagga    2760
tttttattcc aagcgcgctg gggcccacag tcgtacacca cgcagggta gaggactgcg     2820
gccccgagtg cggaatcggg acagctttta tggggttcac                          2860
```

<210> SEQ ID NO 2
<211> LENGTH: 1923
<212> TYPE: DNA
<213> ORGANISM: Porcine endogenous retrovirus
<220> FEATURE:
<221> NAME/KEY: vector
<222> LOCATION: (1)..(61)
<220> FEATURE:
<221> NAME/KEY: primer
<222> LOCATION: (62)..(81)
<220> FEATURE:
<221> NAME/KEY: LTR
<222> LOCATION: (82)..(261)
<220> FEATURE:
<221> NAME/KEY: primer
<222> LOCATION: (232)..(261)
<220> FEATURE:
<221> NAME/KEY: primer
<222> LOCATION: (430)..(449)
<220> FEATURE:
<221> NAME/KEY: primer
<222> LOCATION: (1827)..(1847)
<220> FEATURE:
<221> NAME/KEY: vector
<222> LOCATION: (1827)..(1923)
<220> FEATURE:
<221> NAME/KEY: misc_feature
<222> LOCATION: (3)..(3)
<223> OTHER INFORMATION: n = c, t,g or a
<220> FEATURE:
<221> NAME/KEY: misc_feature
<222> LOCATION: (1420)..(1420)
<223> OTHER INFORMATION: n = c,t,g or a -continued

```
<400> SEQUENCE: 2
canctcggta ccgagctcgg atccactagt aacggccgcc agtgtgctgg aattcgccct      60
tgtgaacccc ataaaagctg tcccgattcc gcactcgggg ccgcagtcct ctacccctgc     120
gtggtgtacg actgtgggcc ccagcgcgct tggaataaaa atcctcttgc tgtttgcatc     180
aagaccgctt ctcatgagtg atttggggtg tcgcctcttc cgagcccgga cgaggggat     240 tgttctttta ctggcctttc accctcagag ctttgtttag actgctgttg cccttgcatg    300
ttagtgctgg gtatccagtc cttattagtg tggttggcga gcaaccctgc ttcccctaga    360
gctttctgcg agactgattt cctttcagtc tcttgctcaa tatggtctct agaagcatct    420
gtgatatatt cccaaatgaa cggcatgaca gctccacggt gtagttacaa tgtttctttc    480
tttctttctc agatcaaaca tcttctatct gtgttaatta ttttcatcaa aatgtacttc    540
cacagctatt ataataattt tacagggaca tagtggacca caaagcccct aaactaggag    600
gctgtgtgcg tgttaccagg tgtgtgggct gaaaagccag gccttctgag actggagcct    660
ggctcagcta aattcgttaa tatcaagtca tttatacatc aactgatcag gtacatcttg    720
agtaagtatg caactatttc tgagtttatt ataacattgt taaagtggtt tatatggctt    780
atatgattta ttctaagcta atatgtccct aagagtacac tgcagtccac tgtgggaggg    840
tcaaaatggg gacagacacg ggaaaatagg aagaggggga atgaagaaaa tacccaggaa    900
tggtgtgact gtgcccaggt tcttggtcac aaccagtcct ggagaaaatg gtcaaacaat    960
gtcaccacaa acccttggtg agtgctcagg atggctttag gcttacagaa cagggagaca    1020
cagtgacagc tccccatgac ctggcaggga acagacagtg agcacccaga actggggcga    1080
ccattgcatg aagaggtgtg ttcatagcac tacagtccac agggccgtgg gatccctcag    1140
cacagcactt actctaagcc tcaatttctc catctgtaaa atggggccat tactagaaat    1200
tcccccaaag ggaccttgtg aaagttaact gtgtaatata cataaaaccc ataaaacagt    1260
gctgagaaca taggattcat taaaaacaaa gaatgggtag acaataaggg tctactgtat    1320
aacacaggga accatatcca atctcctggg gtaaaataaa ccataatgga aaggaatatt    1380
taaaaaacaa aaaaatgtgt aaatgcgtat aataagccan tttgctgtac aacataaatg    1440
aggacaacat tgtaaatcaa ctataactta aaaataataa acaaaaaact caaaaacaaa    1500
taaaaaaaac tgttatcatc atcacatgca gaagaacaga ggcctgagag aaaactactc    1560
gtaaaaccaa aagttcaata ggtcaaccta tggaactgca cttgtctgtg ttgggaggca    1620
ttcgtattac cacacaaata cattaaaagg tttgcagaat ttttttttct cttctaggct    1680
gcaccagtga catatggaag ttccctggga tagggatcga atccaagccg cagccactga    1740
cctacaccac agccatagca acttgggatt caagcttcat ctgcaacctc tgccacagct    1800
ctcagcaata tgggatcgag tcgacgccct atagtgagtc gtattacaag ggcgaattct    1860
gcagatatcc atcacactgg cggccgctcg agcatgcatc tagagggccc aattcgccct    1920
ata                                                                  1923

<210> SEQ ID NO 3
<211> LENGTH: 2528
<212> TYPE: DNA
<213> ORGANISM: Porcine endogenous retrovirus
<220> FEATURE:
<221> NAME/KEY: vector
<222> LOCATION: (1)..(84)
<220> FEATURE:
<221> NAME/KEY: primer
<222> LOCATION: (85)..(105)
```

```
<220> FEATURE:
<221> NAME/KEY: LTR
<222> LOCATION: (106)..(284)
<220> FEATURE:
<221> NAME/KEY: primer
<222> LOCATION: (274)..(284)
<220> FEATURE:
<221> NAME/KEY: primer
<222> LOCATION: (503)..(522)
<220> FEATURE:
<221> NAME/KEY: primer
<222> LOCATION: (2452)..(2472)
<220> FEATURE:
<221> NAME/KEY: vector
<222> LOCATION: (2452)..(2527)

<400> SEQUENCE: 3
cgactcacta tagggcgaat tgggccctct agatgcatgc tcgagcggcc gccagtgtga      60
tggatatctg cagaattcgc ccttgtgaac cccataaaag ctgtcccgat tccgcactcg     120
gggccgcagt cctctacccc tgcgtggtgt acgactgtgg gccccagcgc gcttggaata     180
aaaatcctct tgctgtttgc atcaagaccg cttctcgtga gtgacttggg gtgtcgcctc     240
ttccgagccc ggacgagggg gattgttctt ttactggcct ttcagtagtg tgtgcatgtg     300
cacgtgtgtg catgtgaaga ataagacaaa ttccatcatc agcaagtcac ttaatttctc     360
tggacttcat tttcactccc ataaacagtt atttcttaaa gtattgtaat gattagagaa     420
aatttacttt aaattcttgt cactcagtgg ttaggctctt gtaaaatgtt agttattgtc     480
attcttccgt gagaaatgtt gtctgacttc aattctgttg ctaatctact gagttggatg     540
tggggatgct cattcctatt gactattcat tgaattgaat gttttggatc cagctcctat     600
gtaagaaatc ctttagtaat ctcaaacaca gaaatgagtc caattatgca attaatgatg     660
aaaagtataa atacgtctcc atccgagact gatccttta ggaatacagt caattaaaat     720
gtcttatact aacactttgc ctttcataaa gcctcctggg gaggacattc aaattgccaa     780
gaaattttag catctggtct tgatttccca ccacatctta atgagagact gagcatatat     840
tattttgaaa aaagtttca tttctacatc aaagagaaaa gtagtaaaac cagttgcatg     900
tcttaaatat ttacaaagac acacactcat tccaatgaca ttaaacactg ttattctaga     960
aatatttaag attaagattc tctagttttt acttatccta agatttaaag caaattaatt    1020
cctcattagt tatgaggaat atgctttgaa acaagctgtt tatttttcaa ttggagtgtg    1080
gtgtgccaag caaagcaatt aaacaagagt tgccagcaaa atcagcagcc agccactgg    1140
aagacaagag caataaccta ctgatgactt cctattctgt ttttagccat gttcttataa    1200
aaaagaaat atgtgtgtat gtgtgtgtgt atagaaactg tatttcactc acataaataa    1260
ccaaatgggt tcaaaaagtt atcattctat gaataacata taatagcatg tctgaaaaga    1320
ttaactacaa ctatagagaa tgcacgcatg atccaaaggg tgatcagtgt acaaggcata    1380
tgcttaatat aaaaagatag atattagccc aggaatagac acacacaaaa tcttctgata    1440
ataatgagac atttgatgta ccatttataa atatcagatg ccacaaacaa catccgatag    1500
catacatata cttacaagaa gctgtgtttt atgtagcggc attttgttgc tggtttaaag    1560
taaactcaca ggcaaagtac tgtcaagaat gaaaaaactg cactcattcc ttgagactac    1620
ctcttagaac taaaaacaag tcatccaaag gatgatattt gggccaaatt tgaatatgtg    1680
gctaatattt cttatttttt ttctttagac tcaaaagaaa atgtaatgct ttccagattg    1740
agacatatgt accttacaca tggcactcgg cattaccatc tgtgccacaa acataataag    1800
taggctgcct gacataaaca gcagggata aatgaggttt tcatgtctct acctttctct    1860
```

-continued

```
gcacaaagtc ttttctgaga tagggtgttc tctgttcccg aaaactaggt gggatattag    1920
agtttcctgt ccagtgactc ctggtgttca actatttccc ttgacttgat ttctgcttaa    1980
ttaaaagaat aaatattata gagctacaaa ataaataaaa cactggtgta ttttcacat     2040 taagttgagc aatttgtgta cttttgacag ttcaatctta aattcaaatt cccttccccc    2100
accataaatt aaggagcata tattgccatc tagtgtcctt ctgaagcaac acatctacca    2160
ggatcatgaa agaaaacatg ttacattaga cagaggatgt aaaaatggta caagtaggta    2220
atttggattt gtgtaatata tcaaaacact tttagtgaaa actgatagag taaagtgtct    2280
taagatcact gctttcaaca tttcaactga aagatacaag gtgttccaga tttgcttaat    2340
taggaagcat ggtgatgtca tctgtgaccc aggagcttcc atcttaccac tcagcatctt    2400
cataatgttg atcttaattc ccaggcatat gccctcagga tcgagtcgac gccctatagt    2460
gagtcgtatt acaagggcga attccagcac actggcggcc gttactaggg atccgagctc    2520
ggtaccaa                                                             2528
```

```
<210> SEQ ID NO 4
<211> LENGTH: 1224
<212> TYPE: DNA
<213> ORGANISM: Porcine endogenous retrovirus
<220> FEATURE:
<221> NAME/KEY: vector
<222> LOCATION: (1)..(141)
<220> FEATURE:
<221> NAME/KEY: misc_feature
<222> LOCATION: (713)..(713)
<223> OTHER INFORMATION: n = c,t,g or a
<220> FEATURE:
<221> NAME/KEY: primer
<222> LOCATION: (142)..(163)
<220> FEATURE:
<221> NAME/KEY: LTR
<222> LOCATION: (164)..(262)
<220> FEATURE:
<221> NAME/KEY: primer
<222> LOCATION: (246)..(262)
<220> FEATURE:
<221> NAME/KEY: primer
<222> LOCATION: (936)..(956)
<220> FEATURE:
<221> NAME/KEY: vector
<222> LOCATION: (1127)..(1224)
<220> FEATURE:
<221> NAME/KEY: primer
<222> LOCATION: (1127)..(1145)
<220> FEATURE:
<221> NAME/KEY: misc_feature
<222> LOCATION: (722)..(722)
<223> OTHER INFORMATION: n = c,t,g or a
<220> FEATURE:
<221> NAME/KEY: misc_feature
<222> LOCATION: (831)..(831)
<223> OTHER INFORMATION: n = c,t,g or a
<220> FEATURE:
<221> NAME/KEY: misc_feature
<222> LOCATION: (835)..(835)
<223> OTHER INFORMATION: n = c,t,g or a

<400> SEQUENCE: 4
ccagcttggt accgagctcg gatcccctagt aacggccgcc agtgtgctgg aattcgccct     60
tgtgaacccc ataaaagctg tcccgattct gcactcgggg ccgcagtcct ctacccctgc    120
gtggtgtacg actgtgggcc ccagcgcgct tggaataaaa atcctcttgc tgtttgcatc    180
aagaccgctt ctcgtgagtg atttagggtg tcgcctcttc cgagcccgga cgaggggat     240 tgttcttata ctggccttc atgacaatcc atagtaaaag taaataatc ccattgcttt      300
```

-continued

```
ttcttaatga ataaaagttt tgagcatgaa taacattttg agaaaaaatg tacttttttct    360 tttgggaaac ggctgttttc aattgaattg ttattaacct tttcatatta atttatagaa    420 gcattttttgt tttggttatg tgtgtatcaa ctattgactc ccaggttttg gtctaaattt    480
tcttttttct cgatattttt tgatgagcag aacctctaaa ttttaatgca gccaaattga    540
tatttaaggt agtacttact ctatgtttgt ttttttttgtt ttttttttttt ttgtcttttg    600 tctttttgtc ttttgttgtt gttgttgttg ctatttcttg ggccgctccc gcagcatatg    660
gaggttccca ggctaggggt ccaatcggag ctgtagcctc cggcctacgc canagccaca    720
gnaacgcggg atccgagccg cgtctgcaac ctacaccaca gctcacggca acgccggatc    780
gttaacccac tgagcaaggg cagggaccga acccgcaacc tcatggttcc ntagncggat    840
tcgttaacca ctgcgccacg acgggaactc ctatagtctt aatatattct tctcacactgc    900 cctctaaagt tttaaatttt acttgtagaa tttgggtgtt tcatttatca tgagttaatt    960
tttttaatta tgtaaatact tattcattat tcctctatag ataatcataa aagtaatgaa   1020
aacttcatcc tttcccaaat gatctacaat acctattcca tcattaatca agtgttcata   1080
caaaggtata tctggtttta tactgtgcaa tatgatcgag tcgacgccct atagtgagtc   1140
gtattacaag ggcgaattct gcagatatcc atcacactgg cggccgctcg agcatgcatc   1200
tagagggccc aattcgccct atag                                           1224
```

<210> SEQ ID NO 5
<211> LENGTH: 1976
<212> TYPE: DNA
<213> ORGANISM: Porcine endogenous retrovirus
<220> FEATURE:
<221> NAME/KEY: vector
<222> LOCATION: (1)..(54)
<220> FEATURE:
<221> NAME/KEY: primer
<222> LOCATION: (55)..(75)
<220> FEATURE:
<221> NAME/KEY: LTR
<222> LOCATION: (76)..(504)
<220> FEATURE:
<221> NAME/KEY: primer
<222> LOCATION: (486)..(504)
<220> FEATURE:
<221> NAME/KEY: primer
<222> LOCATION: (1676)..(1695)
<220> FEATURE:
<221> NAME/KEY: primer
<222> LOCATION: (1704)..(1733)
<220> FEATURE:
<221> NAME/KEY: vector
<222> LOCATION: (1704)..(1976)

<400> SEQUENCE: 5

```
ggtaccgagc tcggatccct agtaacggcc gccagtgtgc tggaattcgc ccttgacagc     60
ttttatgggg ttcacaacaa agcctgtgtg tcacaaacca atcatttaa aatatcgaga    120 gcccgcgctc cgtggaccaa tcatcttaaa atatcgagag cccgcgctcc gtggaccaat    180 catttttaaaa tagctccgga ggtccgcatc tgcgtgggct cctgggcaga gtgacagatt    240
gcagttgaga taggtcacta gggctgtcaa tgtgtaatca attcttctat ggtgccagtc    300
agttttacag aatccagata agcgattagt caactcattt cctgttatct tacttaggcc    360
aggatagcag gccctggaac aataggaagt gtgaccttct acctatttac tggcagccag    420
cagggtctgg aattcggggg catttagagc ttttttattaa cttcctgggt tctgggaggg    480
ttaggttgca ttttcatcct ttcagtcaaa aattaaagtg cttcaaaata gcatatgtta    540
```

-continued

```
gagaaaatgt atatggaggg gatgcttata cattgctgct taaaatataa attggtataa    600
tcagtttaga aaataatttg atgttattat ggaaaattgc cttatcatat atagtaaatt    660
ccagaaattt cactccacaa tatttacctg agagaaaatc ttgcacatgt gaaccagagc    720
agatacacaa gagttatcta taatatcatg gttttttaata acaaaatttg tctttaaaaa    780
ataacacata cacactactc tataaaatag ataattaaca cgaacctact atatagcaca    840
gggaatttac acaacagttt ctaaaaatct acattggaaa taatggatgt atgtgtatgc    900
ataactgatt tactttgctg tacacttgaa actaatacaa cattgtaagt caactatact    960
ccaataaaat taaaaaaaaa aagaaaaac aaaagaaat aaccaaatgt gaaaacaatg   1020
gataagtgaa caaattgtac tatggtcaat tttacaagac tggattagga gagtaacatc   1080
atcaatatag taatatagat cacctctgac ttcagtcctt ctcataaaag aaaaactagc   1140
aactatctga gaaaattcca gagcccccag gtgaggctga aacacccttc tgcataagaa   1200
agacctacaa gtactgcatt acaaggaatc attacatttt aaccacgttg tccttcttcc   1260
aggacagcac agcacaccag tgagaggctc tctgggcctc tggcttctct ctgggaaaaa   1320
gagaatccaa aatgggtatt cagcttcccc agcattggag gattcttcag aaggctcact   1380
tgggtcctat ttcctgggga atcactggag aatctgcaga acttaagcac tgagtatcag   1440
atagaggcaa ttaaatggca tggcctacat caactggtac tcagatattt gcagactaca   1500
ttcctgcttg cagtggtgtc taagcaagga tctcaaccag cagctttgtc catctgcaga   1560
ttccagtcag tggccctgta tggccaagga gttgggttgg cagctctgca tgttttgggt   1620
cttcagtcaa tgggttgtac cctccatgga acctttctt caattcagcc caattgctga   1680
gcatagtctc catccagttt catccctata ggatgtgtgg ccatagattc tcagtactgc   1740
gaagcacatc tttagacaa gggatgggca agggaacaaa ttcacagttc cacccaacaa   1800
cttagcataa gctccagtta cgaggctatg gcctctgaag agcatggcca cagaccagcc   1860
cgggccgtcg accacgcgtg ccctatagtg agtcgtatta caagggcgaa ttctgcagat   1920
atccatcaca ctggcggccg ctcgagcatg catctagagg gcccaattcg ccctat   1976
```

<210> SEQ ID NO 6
<211> LENGTH: 695
<212> TYPE: DNA
<213> ORGANISM: Porcine Endogenous Retrovirus
<220> FEATURE:
<221> NAME/KEY: vector
<222> LOCATION: (1)..(106)
<220> FEATURE:
<221> NAME/KEY: primer
<222> LOCATION: (86)..(106)
<220> FEATURE:
<221> NAME/KEY: primer
<222> LOCATION: (130)..(149)
<220> FEATURE:
<221> NAME/KEY: primer
<222> LOCATION: (195)..(210)
<220> FEATURE:
<221> NAME/KEY: LTR
<222> LOCATION: (195)..(624)
<220> FEATURE:
<221> NAME/KEY: primer
<222> LOCATION: (625)..(647)
<220> FEATURE:
<221> NAME/KEY: vector
<222> LOCATION: (648)..(695)
<220> FEATURE:
<221> NAME/KEY: misc_feature
<222> LOCATION: (2)..(2)
<223> OTHER INFORMATION: n = c,t,g or a

```
<220> FEATURE:
<221> NAME/KEY: misc_feature
<222> LOCATION: (4)..(4)
<223> OTHER INFORMATION: n = c,t,g or a

<400> SEQUENCE: 6
tncnactcct ataggggcgaa ttgggccctc tagatgcatg ctcgagcggc cgccagtgtg      60
atggatatct gcagaattcg cccttgtaat acgactcact ataggggcacg cgtggtcgac     120 gcccgggctg gtctgtgacc tactccatag ctgtagcaac actggatcct aacccacca      180 ttccacagca ggaactgaaa ggatgaaaat gcaacctaac cctcccagaa cccaggaagt      240
taataaaaag ctctaaatgc ccccgaattc cagaccctgc tggctgccag taaataggta     300
gaaggtcaca cttcctattg ttccagggcc tgctatcctg gcctaagtaa gataacagga      360
tatgagttga ctaattgctt atctggattc tgtaaaactg actggcacca tagaagaatt     420
gattacacat tgacagccct agtgacctat ctcaactgca atctgtcact ctgcccagga     480
gcccacgcag atgcggacct ccggagctat tttaaaatga ttggtccacg gagcgcgggc     540
tctcgatatt ttaaaatgat tggtccacgg agcgcgggct ctcgatattt taaaatgatt    600
ggtttgtgac gcacaggctt tgttgtgaac cccataaaag ctgtcaaggg cgaattccag     660
cacactggcg gccgttacta gtggatccga gctcg                                 695

<210> SEQ ID NO 7
<211> LENGTH: 1150
<212> TYPE: DNA
<213> ORGANISM: Porcine endogenous retrovirus
<220> FEATURE:
<221> NAME/KEY: vector
<222> LOCATION: (1)..(73)
<220> FEATURE:
<221> NAME/KEY: primer
<222> LOCATION: (53)..(73)
<220> FEATURE:
<221> NAME/KEY: primer
<222> LOCATION: (617)..(636)
<220> FEATURE:
<221> NAME/KEY: LTR
<222> LOCATION: (872)..(1050)
<220> FEATURE:
<221> NAME/KEY: primer
<222> LOCATION: (872)..(900)
<220> FEATURE:
<221> NAME/KEY: primer
<222> LOCATION: (1051)..(1071)
<220> FEATURE:
<221> NAME/KEY: vector
<222> LOCATION: (1072)..(1150)

<400> SEQUENCE: 7
accgagctcg gatccactag taacggccgc cagtgtgctg gaattcgccc ttgtaatacg      60
actcactata gggcacgcgt ggtcgacggc ccgggctggt ctgctgccac catcatgtcc     120
aggagagaag aaccagaggg actaaaaggt gagacagcc acaaaacaat caggagaatg      180
cttctaacaa aatataaact tcaggcatgt cagttgggag agtcatctca gaggaaacca     240
aatcaatttc actaagacct taatggttgc caagatgatt tttataatac agattatttg      300
ataggtaaaa tcacccttta ctatgcttac tattatgaga aaaataggac aactatgtat     360
agttgcaaaa gtaatctttc tgaagtatga tttttttctt ttcttcttct tcttcttttt      420 ttttttttg tcttttttgcc ttttctaggg ccactccctt ggcatatgaa ggttcccagg      480
ctaggggtct aattggagct gtagccgcca gcctacacca gagccacagc aacggggat     540 ccttaaccca ctgagcaagg ccagggatca aacccaaaac ttcatggttt ctagtcggat     600
```

```
ttgttaaccg ctgcgccatg acggcaactc ctgaagtatg attttttca tgtttccccc      660 gtagtctcca ttctccccct acgatttatt atatagctat gtaataaaca gaagatatat     720
attaatttga tagtcactat ataaattagg ggaatacatt ttaataattc atatttacct     780
aacaacaatt ctaaaactta gaaaaatcaa ctaacttgtc caagattata gccaggtgca     840
ctaggaagaa aaccaatgct tccaggagtt ctgaaaggcc agtaaaagaa caatcccccct    900 cgtccgggct cggaagaggc gacaccccaa atcactcacg agaagcggtc ttgatgcaaa    960
cagcaagagg attttttattc caagcgcgct ggggcccaca gtcgtacacc acgcaggggt   1020
agaggactgc ggccctgagt gcggaatcgg gacagctttt atggggttca caagggcgaa   1080
ttctgcagat atccatcaca ctggcggccg ctcgagcatg catctagagg gcccaattcg   1140
ccctatagga                                                            1150
```

<210> SEQ ID NO 8
<211> LENGTH: 2526
<212> TYPE: DNA
<213> ORGANISM: Porcine endogenous retrovirus
<220> FEATURE:
<221> NAME/KEY: vector
<222> LOCATION: (1)..(101)
<220> FEATURE:
<221> NAME/KEY: primer
<222> LOCATION: (81)..(101)
<220> FEATURE:
<221> NAME/KEY: primer
<222> LOCATION: (1976)..(1998)
<220> FEATURE:
<221> NAME/KEY: LTR
<222> LOCATION: (2268)..(2447)
<220> FEATURE:
<221> NAME/KEY: primer
<222> LOCATION: (2268)..(2280)
<220> FEATURE:
<221> NAME/KEY: primer
<222> LOCATION: (2448)..(2468)
<220> FEATURE:
<221> NAME/KEY: vector
<222> LOCATION: (2469)..(2526)

<400> SEQUENCE: 8

```
ctcctatagg gcgaattggg ccctctagat gcatgctcga gcggccgcca gtgtgatgga     60
tatctgcaga attcgccctt gtaatacgac tcactatagg gcgtcgactc gatcctgagg    120
gcatatgcct gggaattaag atcaacatta tgaagatgct gagtggtaag atggaagctc    180
ctgggtcaca gatgacatca ccacgcttcc taattaagca aatctggaac accttgtatc    240
tttcagttga atgttgaaa gcagtgatct taagacactt tactctatca gttttcacta    300
aaagtgtttt gatatattac acaaatccaa attaccact tgtaccattt ttacatcctc    360
tgtctaatgt aacatgtttt ctttcatgat cctggtagat gtgttgcttc agaaggacac    420
tagatggcaa tatatgctcc ttaatttatg gtggggaag ggaatttgaa tttaagattg     480
aactgtcaaa agtacacaaa ttgctcaact taatgtgaaa aatacaccag tgttttattt    540
attttgtagc tctataatat ttattctttt aattaagcag aaatcaagtc aagggaaata    600
gttgaacacc aggagtcact ggacaggaaa ctctaatatc ccacctagtt ttcgggaaca    660
gagaacaccc tatctcagaa aagactttgt gcagagaaag gtagagacat gaaaacctca    720
tttatcccct gctgtttatg tcaggcagcc tacttattat gtttgtggca cagatggtaa    780
tgccgagtgc catgtgtaag gtacatatgt ctcaatctgg aaagcattac attttctttt    840
gagtctaaag aaaaaaaaata agaaatatta gccacatatt caaatttggc ccaaatatca    900
```

-continued

```
tcctttggat gacttgtttt tagttctaag aggtagtctc aaggaatgag tgcagttttt      960
tcattcttga cagtactttg cctgtgagtt tactttaaac cagcaacaaa atgccgctac     1020
ataaaacaca gcttcttgta agtatatgta tgctatcgga tgttgtttgt ggcatctgat     1080
atttataaat ggtacatcaa atgtctcatt attatcagaa gattttgtgt gtgtctattc     1140
ctgggctaat atctatcttt ttatattaag catatgcctt gtacactgat cacccttttgg   1200 atcatgcgtg cattctctat agttgtagtt aatcttttca gacatgctat tatatgttat    1260
tcatagaatg ataactttt gaacccattt ggttatttat gtgagtgaaa tacagtttct     1320
atacacacac acatacacac atatttcttt ttttataaga acatggctaa aaacagaata    1380
ggaagtcatc agtaggttat tgctcttgtc ttccagtggc tgggctgctg attttgctgg    1440
caactcttgt ttaattgctt tgcttggcac accacactcc aattgaaaaa taaacagctt    1500
gtttcaaagc atattcctca taactaatga ggaattaatt tgctttaaat cttaggataa    1560
gtaaaaacta gagaatctta atcttaaata tttctagaat aacagtgttt aatgtcattg    1620
gaatgagtgt gtgtctttgt aaatatttaa gacatgcaac tggttttact acttttctct    1680
ttgatgtaga aatgaaactt tttttcaaaa taatatatgc tcagtctctc attaagatgt    1740
ggtgggaaat caagaccaga tgctaaaatt tcttggcaat ttgaatgtcc tccccaggag    1800
gctttatgaa aggcaaagtg ttagtataag acattttaat tgactgtatt cctaaaagga   1860
tcagtctcgg atggagacgt atttatactt ttcatcatta attgcataat tggactcatt    1920
tctgtgtttg agattactaa aggatttctt acataggagc tggatccaaa acattcaatt    1980
caatgaatag tcaataggaa tgagcatccc cacatccaac tcagtagatt agcaacagaa    2040
ttgaagtcag acaacatttc tcacggaaga atgacaataa ctaacatttt acaagagcct    2100
aaccactgag tgacaagaat ttaaagtaaa ttttctctaa tcattacaat actttaagaa    2160
ataactgttt atgggagtga aaatgaagtc cagagaaatt aagtgacttg ctgatgatgg    2220
aatttgtctt attcttcaca tgcacacacg tgcacatgca cacactactg aaaggccagt    2280
aaaagaacaa tccccctcgt ccgggctcgg aagaggcgac accccaagtc actcacgaga    2340
agcggtcttg atgcaaacag caagaggatt tttattccaa gcgcgctggg gcccacagtc    2400
gtacaccacg caggggtaga ggactgcggc cccgagtgcg gaatcgggac agcttttatg    2460
gggttcacaa gggcgaattc cagcacactg gcggccgtta ctagtggatc cgagctcggt    2520
accaag                                                               2526
```

PERV SCREENING METHOD AND USE THEREOF

FIELD OF THE INVENTION

The invention relates to porcine endogenous retrovirus (PERV) and novel methods of identification, isolation and screening via polynucleotide flanking sequences. It also relates to use of said polynucleotide flanking sequences in methods of providing a pig that does not express a porcine endogenous retrovirus. The organs, tissues and cells of said pig being capable of use for xenotransplantation.

BACKGROUND OF THE INVENTION

A shortage of human organs for transplantation has led to an interest in xenotransplantation using alternative non-human species such as the pig for transplantation. Studies of humans treated with living pig tissue to date have not found any evidence of PERV infection (Paradis et al 1999, Heneine et al 1998, Patience et al 1998, Pitkin and Mullon 1999, Schumaker et al 2000, Levy et al 2000, reviewed in Herring et a, 2001 and Cunningham et al 2001). These studies have included patients with a range of exposure routes to pig tissues, including skin grafts, transplantation with porcine pancreatic islets, and extracorporeal liver and splenic perfusion. Examination of primates transplanted with pig endothelial cells has also shown absence of infection with PERV, despite the analysis of multiple tissue types (Martin et al 1999), despite it being possible to infect non-human primate cells in vitro (Blusch et al 2000).

Despite the lack of evidence of PERV infection in humans, it would be desirable to use organ source pigs that gave the lowest possible zoonotic risk. Bosch et al (2000) found that most expressed PERV proviruses were defective, in common with endogenous retroviruses in other species such as humans, mice and cats (Tonjes et a/1999). Although some pig to pig variation in proviral distribution has been found (Jin et al 2000, Bosch et al 2000), some proviruses are likely to be common to all pigs. No systematic study has yet been published to determine which proviruses are intact, and what degree of pig to pig variance intact PERV proviruses have. Provirus expression patterns vary between different cell types (Langford et al 2001), or may be altered due to cryptic stimuli during organ rejection. Cloning of pigs by nuclear transfer is being actively explored as a method to generate genetically modified pigs for xenotransplantation (Polejaeva et al 2000).

Breeding pigs under specific or qualified pathogen-free conditions is generally assumed to reduce the risk of transmitting exogenous viral, bacterial, fungal and parasitic agents by xenotransplantation. However, microorganisms such as porcine endogenous retrovirus can be stably transmitted in the germ line and therefore cannot be easily eliminated. Many of the unique properties of retroviruses are due to the synthesis of a complement DNA copy from the RNA template via reverse transcriptase and integration of this DNA into the host genome. The integrated retroviral copy which is referred to as an endogenous copy or "provirus" can be transmitted via the germ line. Although many proviruses are defective and unable to replicate, if the provirus is intact, it can be activated by certain stimuli and then initiate viral replication using the host's cellular mechanisms. Replication of the virus may result in viremia, malignant transformation (e.g. via insertion of retroviral oncogenes), degeneration or other insertional effects (e.g. gene inactivation).

There is a clear need for a method of identification, isolation and screening for such retroviruses as porcine endogenous retrovirus. Further, such a method should be capable of being used in a rapid and efficient manner to screen herds of animals.

DESCRIPTION OF THE INVENTION

The present invention relates to porcine endogenous retrovirus (PERV) and novel methods of identification, isolation and screening via polynucleotide flanking sequences. It also relates to use of said polynucleotide flanking sequences in methods of providing a pig that does not express a porcine endogenous retrovirus. The organs, tissues and cells of said pig being capable of use for xenotransplantation.

The present invention relates to porcine endogenous retrovirus polynucleotide sequences known as "flanking sequences". Flanking sequences are DNA sequences surrounding a porcine endogenous retrovirus which represent a unique molecular signature that can be used to characterize PERV integration sites and identify PERVs. Flanking sequences of the present invention are, for example, isolated polynucleotides and fragments thereof selected from the group consisting of SEQ. ID NO.1-8 as herein described.

The present invention relates to the PERV family of retrovirus of which three main classes have been identified to date: PERV A, B and C (Patience et al 1997, Akiyoshi et al 1998), the gag and pol genes of which are highly homologous, and they differ principally in the LTRs and env hypervariable regions. PERV A and B are ubiquitous in domestic pigs, however, large white pigs that do not have PERV C have been identified (Bosch et al 2000, Jin et al 2000). Domestic pigs have up to 50 copies of PERV as measured using a probe on Southern blots (Patience et al 1997). Analysis of infection and pseudotyping experiments has shown that PERV A, B and C probably use different receptors (Takeuchi et al 1998, Wilson et al 2000), although these have yet to be cloned. PERV A and B productively infect a wide range of cell types from both humans and other mammals, while PERV C has a more restricted tropism, among human cells examined only infecting the HT1080 cell line non-productively (Takeuchi et al 2000). PERV released from pig tissues such as PBMCs, endothelial cells and pancreatic islets have been shown to infect human cell lines, including 293 and endothelial cells (Martin et al 2000, Takeuchi et al 1998, Wilson et al 2001).

Identification of PERVs

The identification of PERV is technically challenging since identification of PERVs is hindered by the presence of long (about 700 bp) identical LTR sequences at both 5' and 3' termini of a porcine endogenous retrovirus, and indeed all retroviral proviruses. This precludes straightforward upstream or downstream primer sequencing from, for example, a cosmid or lambda clone harbouring the provirus.

One aspect of the invention described herein is a novel and more rapid method of identifying porcine endogenous retrovirus using polynucleotide flanking sequences. The PERV-specific flanking sequences are preferably identified by linker-mediated PCR. Using linker-mediated PCR, unique proviral loci from porcine endogenous retrovirus-positive cosmid and lambda library DNA clones are identified. Such porcine endogenous retrovirus flanking DNA sequence information is essential for establishing prevalence of PERV within a host mammal.

Screening for PERVs

The rapid and effective technique according to the present invention described herein is valuable for screening large numbers of DNA library clones in parallel. Briefly, genomic library clones containing proviruses are digested with blunt cutting restriction enzymes, double stranded DNA linker molecules are ligated and the mixture diluted and used as a template for PCR.

The PCR product size is defined by the restriction enzyme site location flanking the provirus which then can be used for the early identification of duplicate porcine endogenous retrovirus-positive clones in the library. This approach leads to the establishment of proviral fingerprints in genomic DNA such that novel integrations resulting from superinfection or retrotransposition can be detected with no subcloning requirement. It also allows for extensive sequencing of large fragments. Linker-mediated PCR is the preferred method for mapping PERVs according to the present invention.

The screening of mammals according to the present invention provides for the elimination and inactivation of donors with known proviruses. The present invention provides for the identification of retroviral sequences, especially porcine endogenous retrovirus, from especially pigs.

One embodiment of the invention relates to a method of screening a pig for the presence of a porcine endogenous retrovirus wherein said method comprises (i) detection of a porcine endogenous retrovirus by at least one polynucleotide, wherein said polynucleotide is an isolated polynucleotide selected from the group consisting of SEQ ID No.1-8 and (ii) identification of a pig which has a porcine endogenous retrovirus.

Another embodiment of the invention relates to a method of screening a pig for the presence of a porcine endogenous retrovirus wherein said method comprises (i) detection of a porcine endogenous retrovirus by at least one polynucleotide, wherein said polynucleotide is a fragment of an isolated polynucleotide selected from the group consisting of SEQ ID No.1-8 and (ii) identification of a pig which has a porcine endogenous retrovirus. Preferred fragments are at least 15 nucleotides in length and extend up to 2000 nucleotides in length. They have substantially the same function as the polypeptide encoded by the reference nucleotide sequence.

A further embodiment of the invention relates to a method of screening a pig for the presence of a porcine endogenous retrovirus wherein said method comprises (i) detection of a porcine endogenous retrovirus by at least one polynucleotide, wherein said polynucleotide is a homologue of the group consisting of SEQ ID No.1-8 and (ii) identification of a pig which has a porcine endogenous retrovirus. Preferably said homologue is a polypeptide having substantially the same structure and function as the polypeptide encoded by the reference nucleotide sequence, e.g. where only changes in amino acids not affecting the polypeptide function occur. Preferably the homologous nucleotide sequence encodes the polypeptide encoded by the reference nucleotide sequence. The percentage of identity between the homologous nucleotide sequence and the reference nucleotide sequence preferably is at least 80%, more preferably at least 85%, preferably at least 90%, more preferably at least 95%, still more preferably at least 99%.

Another embodiment of the invention relates to the use of at least one polynucleotide of the group consisting of SEQ ID No. 1-8 in screening a pig for the presence or absence of a porcine endogenous retrovirus at a particular chromosomal position.

Providing a Pig Modified Not to Express a Selected PERV

The polynucleotide sequences disclosed in the present invention (SEQ ID No.1-8) can be used to design a porcine endogenous retrovirus-specific gene-targeting construct to 'knock out' the locus by homologous recombination. The ability to clone animals using nuclear transfer from somatic cells manipulated in vitro is key to the practicality of this knock-out approach (Wolf et al., (1998), McCreath et al. (2000)).

One embodiment of the present invention is to a method of providing a pig modified not to express a selected porcine endogenous retrovirus comprising (i) identification of a porcine endogenous retrovirus by at least one polynucleotide sequence selected from the group consisting of SEQ ID. No.1-8 (ii) knock-out or inactivation by homologous recombination of said porcine endogenous retrovirus and (iii) selection of a pig which does not express said porcine endogenous retrovirus.

Another embodiment of the present invention is to a method of providing a pig modified not to express a selected porcine endogenous retrovirus comprising (i) identification of a porcine endogenous retrovirus by at least one polynucleotide sequence fragment wherein said polynucleotide is a fragment of an isolated polynucleotide selected from the group consisting of SEQ ID No.1-8 (ii) knock-out or inactivation by homologous recombination of said porcine endogenous retrovirus and (iii) selection of a pig which does not express said porcine endogenous retrovirus.

A further embodiment of the present invention is to a method of providing a pig modified not to express a selected porcine endogenous retrovirus comprising (i) identification of a porcine endogenous retrovirus by at least one polynucleotide sequence which is homologous to a polynucleotide selected from the group consisting of SEQ ID. No.1-8 (ii) knock-out or inactivation by homologous recombination of said porcine endogenous retrovirus and (iii) selection of a pig which does not express said porcine endogenous retrovirus. The percentage of identity between the homologous nucleotide sequence and the reference nucleotide sequence is preferably at least 80%, more preferably at least 85%, preferably at least 90%, more preferably at least 95%, still more preferably at least 99%.

In another aspect of the present invention, a vector is provided, consisting of at least one isolated polynucleotide selected from the group consisting of SEQ ID No1-8. In a further aspect of the present invention, a vector is provided consisting of a fragment of a polynucleotide selected from the group consisting of SEQ ID. No.1-8. Finally, a vector is provided according to the present invention consisting of a homologue to a polynucleotide selected from the group consisting of SEQ ID. No.1-8.

Pigs which do not express a selected porcine endogenous retrovirus may be provided by the methods of the present invention. Further, cell, tissue or organ samples taken from said pigs may be used in xenotransplantation.

In another embodiment of the present invention, a detection kit for the detection of porcine endogenous retrovirus comprising (i) detection of a porcine endogenous retrovirus using an isolated polynucleotide sequence wherein said sequence is selected from the group SEQ ID No.1.-8 and fragments and homologues of said sequences.

In practising the present invention, many conventional techniques in molecular biology, microbiology, and recombinant DNA are used. These techniques are well known and are explained in, for example, Current Protocols in Molecular Biology, Volumes I, II, and III, 1997 (F. M. Ausubel ed.); Sambrook et al., 1989, Molecular Cloning: A Laboratory Manual, Second Edition, Cold Spring Harbor Laboratory Press, Cold Spring Harbor, N.Y.; DNA Cloning: A Practical Approach, Volumes I and II, 1985 (D. N. Glover ed.); Oligonucleotide Synthesis, 1984 (M. L. Gait ed.); Nucleic Acid Hybridization, 1985, (Hames and Higgins); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; the series, Methods in Enzymology (Academic Press, Inc.); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively).

In its broadest sense, the term "homologous", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the homologous nucleotide sequence encodes the polypeptide encoded by the reference nucleotide sequence. The percentage of identity between the homologous nucleotide sequence and the reference nucleotide sequence desirably is at least 80%, more desirably at least 85%, preferably at least 90%, more preferably at least 95%, still more preferably at least 99%. Sequence comparisons are carried out using a Smith-Waterman sequence alignment algorithm (see e.g. Waterman, M.S. Introduction to Computational Biology: Maps, sequences and genomes. Chapman & Hall. London: 1995. ISBN 0412-99391-0, or on the World Wide Web at the following address:—hto.usc.edu/software/segaln/index.html). The locals program, version 1.16, is used with following parameters: match: 1, mismatch penalty: 0.33, open-gap penalty: 2, extendedgap penalty: 2. A nucleotide sequence "homologous" to reference nucleotide sequence hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C., with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C., yet still encodes a functionally equivalent gene product.

A "host cell," as used herein, refers to a prokaryotic or eukaryotic cell that contains heterologous DNA that has been introduced into the cell by any means, e.g., electroporation, calcium phosphate precipitation, microinjection, transformation, viral infection, and the like.

"Heterologous" as used herein means "of different natural origin" or represent a non-natural state. For example, if a host cell is transformed with a DNA or gene derived from another organism, particularly from another species, that gene is heterologous with respect to that host cell and also with respect to descendants of the host cell which carry that gene. Similarly, heterologous refers to a nucleotide sequence derived from and inserted into the same natural, original cell type, but which is present in a non-natural state, e.g. a different copy number, or under the control of different regulatory elements.

A "vector" molecule is a nucleic acid molecule into which heterologous nucleic acids may be inserted which can then be introduced into an appropriate host cell. Vectors preferably have one or more origin of replication, and one or more site into which the recombinant DNA can be inserted. Vectors often have convenient means by which cells with vectors can be selected from those without, e.g., they encode drug resistance genes. Common vectors include plasmids, viral genomes, and (primarily in yeast and bacteria) "artificial chromosomes."

"Plasmids" generally are designated herein by a lower case p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated, even if subsequently reintroduced into the natural system. Such polynucleotides could be part of a vector and/or such polynucleotides or polypeptides could be part of a composition, and still be isolated in that such vector or composition is not part of its natural environment.

As used herein, the term "transcriptional control sequence" refers to DNA sequences, such as initiator sequences, enhancer sequences, and promoter sequences, which induce, repress, or otherwise control the transcription of protein encoding nucleic acid sequences to which they are operably linked.

The invention includes "fragments" of any of the nucleic acid sequences disclosed herein. Fragments may be used as a hybridization probe for a cDNA library to isolate the full length gene and to isolate other genes which have a high sequence similarity or similar biological activity. Probes of this type preferably have at least about 30 bases and may contain, for example, from about 30 to about 50 bases, about 50 to about 100 bases, about 100 to about 200 bases, or more than 200 bases. The probe may also be used to identify a cDNA clone corresponding to a full length transcript and a genomic clone or clones that contain the complete PERV gene including regulatory and promoter regions, exons, and introns. An example of a screen comprises isolating the coding region of the PERV gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to. In designing a PCR primer to screen a pig, for example, a minimum of around 15 nucleotides would be used for identifying a PERV. In generating a PERV knock-out construct, a minimum of 500 nucleotides would be used.

In addition to the gene sequences described above, "homologs" of such sequences, as may, for example be present in other species, may be identified and may be readily isolated, without undue experimentation, by molecular biological techniques well known in the art. Further, there may exist genes at other genetic loci within the genome that encode proteins which have extensive homology to one or more domains of such gene products. These genes may also be identified via similar techniques. For example, the isolated differentially expressed gene sequence may be labeled and used to screen a cDNA library constructed from mRNA obtained from the organism of interest. Hybridization conditions will be of a lower stringency when the cDNA library was derived from an organism different from the type of organism from which the labeled sequence was derived. Alternatively, the labeled fragment may be used to screen a genomic library derived from the organism of interest, again, using appropriately stringent conditions. Such low stringency conditions will be well known to those of skill in the art, and will vary predictably depending on the specific organisms from which the library and the labeled sequences are derived. For guidance regarding such conditions see, for example, Sambrook et al. cited above.

Further, a previously unknown differentially expressed gene-type sequence may be isolated by performing PCR using two degenerate oligonucleotide primer pools designed on the basis of amino acid sequences within the gene of interest. The template for the reaction may be cDNA obtained by reverse transcription of mRNA prepared from human or non-human cell lines or tissue known or suspected to express a differentially expressed gene allele.

The PCR product may be subcloned and sequenced to ensure that the amplified sequences represent the sequences of a differentially expressed gene-like nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to screen a genomic library.

PCR technology may also be utilized to isolate full length cDNA sequences. For example, RNA may be isolated, following standard procedures, from an appropriate cellular or tissue source. A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

In cases where the differentially expressed gene identified is the normal, or wild type, gene, this gene may be used to isolate mutant alleles of the gene. Such an isolation is preferable in processes and disorders which are known or suspected to have a genetic basis. Mutant alleles may be isolated from individuals either known or suspected to have a genotype which contributes to PERV disease symptoms. Mutant alleles and mutant allele products may then be utilized in the diagnostic assay systems described below.

A cDNA of the mutant gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant gene to that of the normal gene, the mutation(s) responsible for the loss or alteration of function of the mutant gene product can be ascertained.

Alternatively, a "genomic or cDNA library" can be constructed and screened using DNA or RNA, respectively, from a tissue known to or suspected of expressing the gene of interest in an individual suspected of or known to carry the mutant allele. The normal gene or any suitable fragment thereof may then be labeled and used as a probed to identify the corresponding mutant allele in the library. The clone containing this gene may then be purified through methods routinely practiced in the art, and subjected to sequence analysis as described above.

Additionally, an "expression library" can be constructed utilizing DNA isolated from or cDNA synthesized from a tissue known to or suspected of expressing the gene of interest in an individual suspected of or known to carry the mutant allele. In this manner, gene products made by the putatively mutant tissue may be expressed and screened using standard antibody screening techniques in conjunction with antibodies raised against the normal gene product, as described, below. (For screening techniques, see, for example, Harlow, E. and Lane, eds., 1988, "Antibodies: A Laboratory Manual", Cold Spring Harbor Press, Cold Spring Harbor.) In cases where the mutation results in an expressed gene product with altered function (e.g., as a result of a missense mutation), a polyclonal set of antibodies are likely to cross-react with the mutant gene product. Library clones detected via their reaction with such labeled antibodies can be purified and subjected to sequence analysis as described above.

"Functionally equivalent" may also refer to proteins or polypeptides capable of interacting with other cellular or extracellular molecules in a manner substantially similar to the way in which the corresponding portion of the endogenous differentially expressed gene product would. For example, a "functionally equivalent" peptide would be able, in an immunoassay, to diminish the binding of an antibody to the corresponding peptide (i.e., the peptide the amino acid sequence of which was modified to achieve the "functionally equivalent" peptide) of the endogenous protein, or to the endogenous protein itself, where the antibody was raised against the corresponding peptide of the endogenous protein. An equimolar concentration of the functionally equivalent peptide will diminish the aforesaid binding of the corresponding peptide by at least about 5%, preferably between about 5% and 10%, more preferably between about 10% and 25%, even more preferably between about 25% and 50%, and most preferably between about 40% and 50%.

The differentially expressed gene products may be produced by recombinant DNA technology using techniques well known in the art. Thus, methods for preparing the differentially expressed gene polypeptides and peptides of the invention by expressing nucleic acid encoding differentially expressed gene sequences are described herein. Methods which are well known to those skilled in the art can be used to construct expression vectors containing differentially expressed gene protein coding sequences and appropriate transcriptional/translational control signals. These methods include, for example, in vitro recombinant DNA techniques, synthetic techniques and in vivo recombination/genetic recombination. See, for example, the techniques described in Sambrook et al., 1989, supra, and Ausubel et al., 1989, supra. Alternatively, RNA capable of encoding differentially expressed gene protein sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the differentially expressed gene coding sequences of the invention. Such host-expression systems represent vehicles by which the coding sequences of interest may be produced and subsequently purified, but also represent cells which may, when transformed or transfected with the appropriate nucleotide coding sequences, exhibit the differentially expressed gene protein of the invention in situ. These include but are not limited to microorganisms such as bacteria (e.g., E. coli, B. subtilis) transformed with recombinant bacteriophage DNA, plasmid DNA or cosmid DNA expression vectors containing differentially expressed gene protein coding sequences; yeast (e.g. Saccharomyces, Pichia) transformed with recombinant yeast expression vectors containing the differentially expressed gene protein coding sequences; insect cell systems infected with recombinant virus expression vectors (e.g., baculovirus) containing the differentially expressed gene protein coding sequences; plant cell systems infected with recombinant virus expression vectors (e.g., cauliflower mosaic virus, CaMV; tobacco mosaic virus, TMV) or transformed with recombinant plasmid transformation vectors (e.g., Ti plasmid) containing differentially expressed gene protein coding sequences; or mammalian cell systems (e.g. COS, CHO, BHK, 293, 3T3) harboring recombinant expression constructs containing promoters derived from the genome of mammalian cells (e.g., metallothioneine promoter) or from mammalian viruses (e.g., the adenovirus late promoter; the vaccinia virus 7.5K promoter).

Selection of appropriate vectors and promoters for expression in a host cell is a well known procedure and the requisite techniques for expression vector construction, introduction of the vector into the host and expression in the host per se are routine skills in the art. Generally, recombinant expression vectors will include origins of replication, a promoter derived from a highly-expressed gene to direct transcription of a downstream structural sequence, and a selectable marker to permit isolation of vector containing cells after exposure to the vector.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines which stably express the differentially expressed gene protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the differentially expressed gene protein. Such engineered cell lines may be particularly useful in screening and evaluation of compounds that affect the endogenous activity of the differentially expressed gene protein.

"Gene targeting" is a process by which desired changes are introduced into the nucleotide sequence of a chosen PERV gene of the present invention. Mammalian cells integrate foreign DNA by either a process of non-homologous or homologous recombination. The ability of mammalian cells to mediate recombination between homologous DNA sequences is the basis for gene targeting technology. The entire genome can be potentially manipulated, such that intron sequences or gene promotors or enhancers are equally effective and useful targets as exon sequences.

"Gene therapy" refers to therapy performed by the administration of a nucleic acid to a subject. Any of the methods for gene therapy available in the art can be used according to the present invention. Exemplary methods are described below.

Delivery of the nucleic acid into a subject may be either direct, in which case the subject is directly exposed to the nucleic acid or nucleic acid-carrying vector, or indirect, in which case, cells are first transformed with the nucleic acid in vitro, then transplanted into the patient These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see, e.g., U.S. Pat. No. 4,980,286 and others mentioned infra), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., U.S. Pat. Nos. 5,166,320; 5,728,399; 5,874,297; and 6,030,954, all of which are incorporated by reference herein in their entirety) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188; and WO 93/20221). Alternatively, the nucleic acid can be introduced intracellularly and incorporated within host cell DNA for expression, by homologous recombination (see, e.g., U.S. Pat. Nos. 5,413,923; 5,416,260; and 5,574,205; and Zijlstra et al., 1989, Nature 342:435-438).

In a specific embodiment, a viral vector is used. For example, a retroviral vector can be used (see, e.g., U.S. Pat. Nos. 5,219,740; 5,604,090; and 5,834,182). These retroviral vectors have been modified to delete retroviral sequences that are not necessary for packaging of the viral genome and integration into host cell DNA. The nucleic acid to be used in gene therapy is cloned into the vector, which facilitates delivery of the gene into a patient.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Methods for conducting adenovirus-based gene therapy are described in, e.g., U.S. Pat. Nos. 5,824,544; 5,868,040; 5,871,722; 5,880,102; 5,882,877; 5,885,808; 5,932,210; 5,981,225; 5,994,106; 5,994,132; 5,994,134; 6,001,557; and 6,033,8843, all of which are incorporated by reference herein in their entirety.

Adeno-associated virus (AAV) has also been proposed for use in gene therapy. Methods for producing and utilizing AAV are described, e.g., in U.S. Pat. Nos. 5,173,414; 5,252,479; 5,552,311; 5,658,785; 5,763,416; 5,773,289; 5,843,742; 5,869,040; 5,942,496; and 5,948,675, all of which are incorporated by reference herein in their entirety.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the subject. Recombinant blood cells (e.g., hematopoietic stem or progenitor cells) are preferably administered intravenously. The amount of cells envisioned for use depends on the desired effect, subject state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the subject.

In an embodiment in which recombinant cells are used in gene therapy, a nucleic acid is introduced into the cells such that it is expressible by the cells or their progeny, and the recombinant cells are then administered in vivo for therapeutic effect. In a specific embodiment, stem or progenitor cells are used. Any stem-and/or progenitor cells which can be isolated and maintained in vitro can potentially be used in accordance with this embodiment of the present invention. Such stem cells include but are not limited to hematopoletic stem cells (HSC), stem cells of epithelial tissues such as the skin and the lining of the gut, embryonic heart muscle cells, liver stem cells (see, e.g., WO 94/08598), and neural stem cells (Stemple and Anderson, 1992, Cell 71:973-985).

Epithelial stem cells (ESCs) or keratinocytes can be obtained from tissues such as the skin and the lining of the gut by known procedures (Rheinwald, 1980, Meth. Cell Bio. 21A:229). In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a subject or donor can be grown in tissue culture (Pittelkow and Scott, 1986, Mayo Clinic Proc. 61:771). If the ESCs are provided by a donor, a method for suppression of host versus graft reactivity (e.g., irradiation, drug or antibody administration to promote moderate immunosuppression) can also be used.

With respect to hematopoietic stem cells (HSC), any technique which provides for the isolation, propagation, and maintenance in vitro of HSC can be used in this embodiment of the invention. Techniques by which this may be accomplished include (a) the isolation and establishment of HSC cultures from bone marrow cells isolated from the future host, or a donor, or (b) the use of previously established long-term HSC cultures, which may be allogeneic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration (see, e.g., Kodo et al., 1984, J. Clin. Invest. 73:1377-1384). In a preferred embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., 1977, J. Cell Physiol. 91:335) or Witlock-Witte culture techniques (Witlock and Witte, 1982, Proc. Natl. Acad. Sci. USA 79:3608-3612).

In a specific embodiment, the nucleic acid to be introduced for purposes of gene therapy comprises an inducible promoter operably linked to the coding region, such that expression of the nucleic add is controllable by controlling the presence or absence of the appropriate inducer of transcription.

This invention also relates to the use of isolated polynucleotides (SEQ ID No.1-8) and fragments and homologues thereof of the present invention as diagnostic reagents to be used in a diagnostic kit.

One embodiment of the present invention provides for a detection kit for the detection of a porcine endogenous retrovirus comprising (i) detection of a porcine endogenous retrovirus using an isolated polynucleotide sequence selected from the group consisted of SEQ ID No.1-8 and (ii) identification of a porcine endogenous retrovirus.

Detection which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (e.g., Myers et al., Science (1985) 230:1242). Sequence changes at specific locations may also be revealed by nuclease protection assays, such as RNase and S1 protection or the chemical cleavage method (see Cotton et al., Proc Natl Acad Sci USA (1985) 85: 4397-4401). In another embodiment, an array of oligonucleotides probes comprising nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability (see for example: M. Chee et al., Science, Vol 274, pp 610-613 (1996)).

The embodiment of aspects of the present invention are described by way of examples herein, said examples are not intended in any way to be limiting.

EXAMPLES

Example 1

Preparation of DNA and Linker Molecules

A porcine cosmid genomic DNA library generated from lymphocytic DNA is extracted from a Large White sow and screened for porcine endogenous retrovirus proviruses using both gag and env-specific probes corresponding to regions between nucleotide positions 580 to 2147 and 6681 to 7040 of the Genbank PERV-C (AF038599) and PERV-A (AJ133817) genomes respectively. Double-positive PERV containing cosmid clones are isolated through multiple rounds of screening. Cosmid DNA is purified using the Large-Construct Kit™ (Qiagen) and assayed for gag and env ORF integrity using the protein truncation test (PTT) (Roest et al., (1993)). 2 µg of cosmid DNA is digested with 20 units Pvu II (Roche Biochemicals) in a 20 µl reaction, under standard conditions recommended by the manufacturers, to produce blunt-ended restriction fragments.

Linker molecules consisted of an upper strand oligonucleotide: 5' GTAATACGACTCACTATAGGGCACGCGTGGTCGACGGCCCGGGCTGGT-3' (SEQ ID NO:9) and a shorter lower strand oligonucleotide: 5' AGCAGCCC-NH$_2$-3' (SEQ ID NO:10).

2 µmoles of each oligonucleotide is annealed in 100 µl of 10 mM Tris HCl (pH 8), 50 mM NaCl by heating the mixture to 95° C. for 5 minutes, slowly cooling to 20° C. and maintaining at this temperature for 12 hours. The short oligonucleotide contains an amine group that blocks extension of the 3' end of the linker-ligated genomic fragments, preventing formation of a linker primer (LP) binding site, and therefore a target for PCR amplification without a requirement for the PERV-specific primer binding site on unamplified ligated fragments. In the rare case where the 3' end of the lower oligonucleotide gets extended and produces a LP binding site, intramolecular binding produces a stable and non-extendable panhandle structure between opposite ends of a strand that is favoured over primer annealing. This effect further reduces the risk of generating non-specific PCR products and is known as suppression PCR (Siebert et al., (1995)).

Linker Ligation

To ligate the double stranded linker molecules to the blunt ended restriction fragments 5 µl of Pvu II-digested cosmid DNA from above is added to 3 µl of annealed linker solution, 1 µl 5× ligase buffer (Life Technologies) and 1 µl high concentration DNA ligase (Life Technologies). Ligations are performed at 15° C. for 16 hours.

Linker-molecule Mediated PCR Amplification of Flanking DNA

The ligation mixture is diluted 1:100 with PCR-grade water (Sigma) and 1 µl is used in a PCR reaction using Amplitaq Gold (Perkin Elmer) and 5 pM of sense and antisense primers (Table 1) according to the manufacturers guidelines. Reactions are cycled as follows: 94° C., 9 mins; 94° C., 30 s; 58° C. 30 s; 72° C. 4 mins; 35 cycles in a PE biosystems 2400 thermal cycler. These cycling conditions are known to amplify products up to 7 kb in size.

DNA Sequencing

PCR products are gel purified using the QIAquick Gel Extraction kit (Qiagen) and sequenced directly using the LP primer. Larger fragments are cloned (optional) into pCR2.1-TOPO (Invitrogen) before sequencing with M13 forward and reverse primers. DNA sequencing reactions are carried out using the ABI PRISM Dye terminator Cycle Sequencing Ready Reaction kits (Applied Biosystems) and analysed on the ABI 373 (Applied Biosystems) automated sequencer.

The strategy described above is applied to various unique cosmid clones between 30 and 45 kb in size, each containing a single copy of PERV provirus, as determined by Southern blot with please describe probes env-A and gag DNA probes and RFLP analysis, flanked by unique regions of pig genomic DNA. Two PCR products can be expected for each LTR primer coupled with LP—one consisting entirely of internal PERV DNA and another containing flanking sequence/LTR DNA. For flanking DNA sequence the PCR product size is defined by the proximity of the selected restriction enzyme site upstream or downstream of the provirus LTR. A range of blunt-cutting restriction enzymes is used to increase the likelihood of obtaining a PCR product containing the PERV flanking DNA sequence. Nevertheless, Sma I and Pvu II restriction enzymes are sufficient to obtain flanking sequence for almost all cosmid clones analysed.

The result when this technique is applied to three unique PERV-positive cosmid clones. The cosmid DNA is digested with Pvu II and linker-mediated PCR carried out using the U5 reverse primer. One band represents an internal PERV DNA fragment upstream of the 3' LTR and the other contains 5' flanking DNA. This is confirmed by sequence analysis. The PCR products resulting from Pvu II digest and linker-mediated PCR using the U5 forward primer are evident. In this case, a high molecular weight band (3 kb) contains 2.8 kb of unique 3' flanking DNA as confirmed by sequence analysis. High molecular weight targets amplify less efficiently than their low molecular weight counterparts. Where size margins of PCR products within a reaction are smaller, amplification efficiencies are similar. Using either Sma I or Pvu II it is possible to distinguish internal and external (flanking) PCR products based on size alone for a particular primer pair (LP+U5 forward or LP+U5 reverse) when multiple clones are analysed in parallel. Moreover since the PERV provirus is highly conserved with respect to the flanking DNA, internal band sizes can be predicted and identified based upon PCR product size without the need for cloning and sequencing.

Example 2

Mapping of PERV in a Non-transgenic Large White Pig

Library Preparation and Screening

DNA is extracted from porcine peripheral blood mononuclear cells, and partially digested with Sau3AI according to the vector manufacturers protocol. Libraries are constructed in BamHI digested Lambda Fix II or pSuperCos 1 vectors according to the manufacturers instructions (Stratagene). The cosmid library is screened for PERV A, while the lambda library is screened for PERV B as described below.

For the cosmid library, 3-4 fold genome coverage of clones are plated on LB agar plates supplemented with 50 µg/ml ampicillin. Colonies are grown overnight at 30° C., and lifted onto a Hybond N+ filter (Amersham) to create the master filter. The master filter is then replicated onto three other filters (sets A B and C), which are processed as described in Sambrook et al (1989) and UV crosslinked on a Stratalinker crosslinker (120000 µJ, Stratagene).

The triplicate replica filter sets (sets A, B and C) are screened with probes labelled with $\alpha^{32}$P-dCTP using the Megaprime random primed labelling kit (Amersham Pharmacia Biotech) as follows: filter set A is screened with a probe against PERV gag (sequence AF038600, bases 585-2159), while sets B and C are screened with a probe against PERV A env (sequence Y12238 bases 745-1101). Unincorporated nucleotide is removed by spun column chromatography on Sephadex G50 columns. Filters are prehybridised for three hours at 65° C. in hybridisation buffer containing 6×SSC, 20 mM NaH$_2$PO$_4$, 5× Denhardts solution, 0.4% SDS and 500 µg/ml denatured salmon sperm DNA. Probe is added, and the filters hybridised overnight. Filters is washed once at room temperature in 2×SSC, 0.1% SDS, then twice for 30 min at 65° C. in 0.5×SSC, 0.1% SDS, then twice for 30 min at 65° C. in 0.1×SSC, 0.1% SDS. Filters are either exposed for 24-48 hr to X-ray film at −70° C. with intensifying screens, or for 1-5 hr to a storage phosphor screen, followed by phosphorimaging on a Molecular Dynamics Storm phosphoimager. Phosphorimaged blots are printed onto acetate films prior to alignment on a light box with other relevant filters.

For the lambda Fix II library, a total of 1.5×10$^6$ pfu are plated on NZY agar plates as according to the manufacturers instructions (Stratagene). Duplicate filters are lifted using Hybond NX (Amersham), and denatured and neutralised as described in Sambrook et al (1988). Filters are UV crosslinked as described above and prehybridised for 30 min in Quickhyb solution (Stratagene). Probes are labelled with $\alpha^{32}$P-dCTP using Prime-it II (Stratagene). The gag probe (AF038600, bases 585 to 2159) are added to one filter and the env probe (Y12239 bases 1387 to 1735) to the duplicate filter. Filters are hybridised overnight and then washed as described above for the cosmid filters. Filters are exposed to x-ray film at −70° C. for up to a week and developed using a Compact ×4 automatic film processor (X-ograph Imaging Systems).

Clones that replicated on both the gag and env filters are then purified to homogeneity through multiple rounds of re-screening as described above. This strategy is designed to pick up only full length proviruses. Grossly deleted proviruses that were missing either the entire gag gene, or the VRA and VRB portion of env are thus excluded from further analysis. Clones with smaller deletions or rearrangements are eliminated at later stages as described below. Cosmid DNA is prepared using the Qiagen QIAwell system (Qiagen). Lambda DNA is prepared from liquid lysates as described in Ausubel et at (1987).

1. Primary Analysis

Cosmid and lambda clones are analysed differently, as described below, this is a reflection of the lower yields of lambda DNA relative to cosmid DNA.

Primary analysis of cosmid clones are performed by restriction fragment analysis using SmaI and PvuII digests, to identify clones with identical restriction fragment fingerprints. Representative clones of each RFLP class are further analysed by PCR of open reading frames (ORFs) as described below.

Lambda clones are analysed by restriction digestion with NotI, EcoRI, MsII, SmaI/NotI or AvrII/MsII, followed by Southern blotting (Sambrook et al 1989) onto Hybond NX, and hybridisation with either the $^{32}$P labelled gag and PERV B env probes described above. Southern blots are hybridised as described above. Filters are washed 2×30 min at 65° C. in 1×SSC, 0.1% SDS, and then twice for 30 min at 65° C. in 0.1×SSC, 0.1% SDS, and exposed to x-ray film overnight.

2. Secondary Analysis

The presence of intact viral genes in lambda and cosmid isolates are examined by PCR across the pol open reading frame (ORF), or by PCR of the ORF followed by protein truncation testing (PTT) to analyse the coding potential of the gag and env ORFs. Primers are designed to conserved sequences at the start and end of each ORF, based on published sequence data. PCR conditions are optimised on laboratory generated plasmid clones of PERV C gag, and PERV A, B and C env which had been fully sequenced, and encoded full length ORFs with >98% homology to the published prototype sequences. The pol PCR was optimised on DNA from PK15 cells.

For gag the following primers are used: gag F (5'-GGATC-CTAATACGACTCACTATAGGAACAGAC-CACCATGGGACAGACAGTGACTAC C-3') (SEQ ID NO:11) and gag R(5'-CCCTCCACCTTCAAAGTTAC-3') (SEQ ID NO:12'). 50 µl reactions contained 50 mM KCl, 10 mM Tris-HCI (pH 8.3), 1.5 mM MgCl$_2$ 150 nM each primer, 200 nM each dNTP and 2.5 U Amplitaq (PE Biosystems) with approximately 1 ng cosmid or lambda template. Reactions are then cycled as follows: 95° C. 3 min, 30 cycles of (94° C. 1 min, 60° C. 1 min, 72° C. 1 min 50 s), followed by 10 min at 72° C. PCR is performed in AB12400 or AB19600 thermocyclers (PE Biosystems). For pol, the primers are used: pol F (5'-GGATCCTAATACGACTCACTATAGGAA-CAGACCACCATGGGTGCCACAGGGC AAC-3') (SEQ ID NO:13) and pol R (5'-GACCATTGTCTGACCCGATTA-3') (SEQ ID NO:14). 50 µl reactions contain 50 mM KCI, 10 mMTris-HCI (pH 8.3), 1.5 mM MgCl$_2$ 150 nM each primer, 200 nM each dNTP and 2.5 U Amplitaq (PE Biosystems) with approximately 1 ng cosmid or lambda template. Reactions are then cycled as follows: 95° C. 3 min, followed by 30 cycles of 95° C. 40 s, 58° C. 30 s, 72° C. 3 min, and a final 72° C. 10 min soak.

For env the primers used were: env F (5'-GGATC-CTAATACGACTCACTATAGGAACAGAC-

GACCATGCATCCCACGTTAA GCCG-3') (SEQ ID NO:15') and env R (5'-CGCTCTAGACTAAGCGTAG TCTGGGACGTCGTATGGGTAGAACTGG-GAAGGGTAGAGGTCAGT-3') (SEQ ID NO: 16'). 50 μl reactions are performed under the same conditions as described for gag (above), and then cycled as follows: 95° C. 3 min, 30 cycles of (94° C. 1 min, 62° C. 1 min, 72° C. 2 min 10 s), followed by 10 min at 72° C.

The forward primer sequences shown for gag, pol and env were modified so that they contain a T7 RNA polymerase promoter sequence, such that PCR products from clones giving approximately the predicted product sizes for gag and env can be further analysed by PTT. Additionally the env reverse primer removed the stop codon, and inserted an in-frame HA epitope tag, enabling detection of full length products by Western blotting against the HA tag.

Protein truncation testing for open reading frames is carried out using coupled transcription-translation in rabbit reticulocyte lysate (TNT T7 Rapid for PCR, Promega), with non-radioactive detection using biotinylated-lysine tRNA. Each 25 μl reaction contains: 2.5 μl of unpurified PCR product, 1 μl transcend tRNA (Promega), 20 μl TNT T7 PCR Quick master mix (Promega), supplemented with 20 μM methionine. The reactions are incubated at 30° C. for 90 min, and 2 μl subjected to SDS-PAGE on a 4-12% NuPAGE Bis-Tris gel (Novex/Invitrogen). Gels are semi-dry blotted to Hybond ECL membrane (Amersham Pharmacia Biotech). Biotinylated translation products are detected by blotting with streptavidin-horseradish peroxidase conjugate (1/3750 dilution, Roche), followed by ECL detection (Amersham Pharmacia Biotech). Product sizes are assessed by reference to a translated gag or env plasmid clone of known sequence, and a biotinylated protein molecular weight marker (Roche). HA epitope tagged products are detected by blotting with high-affinity rat anti-HA antisera (1/500, Roche), and a secondary sheep anti-rat HRP conjugate (1/10000, Sigma), followed by ECL detection.

Sequencing Analysis of Cosmid and Lambda Clones.

Clones identified as having full length gag, pol and env genes together with full length gag and env translation products are then sequenced by a combination of methods. Cosmid DNA and PCR products are directly sequenced using using ABI PRISM Dye terminator Cycle Sequencing on an ABI373 (Applied Biosystems), some PCR products are subcloned into pCR2.1 (Invitrogen) prior to sequencing. The lambda clones are directly sequenced using a LICOR 4000 DNA sequencer (MWG Biotech) as follows: 800 ng of lambda DNA is prepared using Thermo sequenase fluorescent labelled sequencing kit (Amersham) according to the manufacturers instructions. The primers used to sequence lambda DNA are described in the table below.

Analysis of Negative Cosmid Clones

Additionally, Southern blots of SmaI digested cosmid DNA are probed with biotin labelled oligonucleotides homologous to the region around the primer binding site (PBS) 5'-biotin GCCTTTCATTTGGTGCGTTGGCCGG-GAAATCCTCGCGACCACCCCTTACAC-3'(SEQ ID NO: 17) (nt 661711, accession no.AJ133817) and the 3'-end of env5'-biotin-ACTGACCTCTAGCCTTCCCAGTTCTAA-GATTAGAACTATTAACAAGACAA-3' (SEQ ID NO: 18) (nt8121-8171, accession no. AJ133817). These probes are external to the probe sequences used in the initial library screening, and to the gag and env PCR primer sets. Southern blotted DNA was prehybridised at 40° C., for 6 hr, then hybridised at 40° C. overnight with 27 nM biotin labelled probe oligo in buffer. The blot was then washed in 1×SSC, 0.1% SDS for 3 times 30 min, at 42° C., then developed with streptavidin horseradish peroxidase conjugate and ECL detection as described for the PTT above. It is assumed that, due to the sequence conservation seen about these regions in all known PERV variants, that failure to bind these oligos would indicate a deleted provirus.

Proviral Flanking Sequence Analysis

Provirus flanking sequence is generated by linker mediated PCR between a primer in the PERV LTR and a primer in a linker ligated onto blunt end cut DNA. Built into this strategy is a suppression effect that reduces the undesirable amplification of doubly adaptor ligated fragments (Siebert et al, 1995). 0.5 μg of PvuII digested cosmid or lambda DNA is ligated to 60 pmol ds adaptor using 10 U T4 DNA ligase (Life Technologies). In a 7 μl reaction for 16-48 hr at 15° C. The adaptor consists of annealed upper strand oligo(5'-GTAATACGACTCACTAT-AGGGCACGCGTGGTCGACGGCCCGGGCTGGT-3') (SEQ ID NO:9 and a 3'-amine blocked lower strand oligo (5'-ACCAGCCC-NH$_2$-3') (SEQ ID NO:10). One microliter of a 1:100 dilution of this reaction is used as template in a 25 μl PCR reaction containing 50 mM KCl, 10 mM Tris-HCl (pH 8.3), 1.5 mM MgCl$_2$ 50 nM LTR specific primer, 50 nM adaptor primer (5'-GTAATACGACTCACTATAGGGC-3') (SEQ ID NO:19), 200 nM each dNTP and 2.5U Amplitaq Gold (PE Biosystems). Reactions is cycled as follows: 94° C. 9 min, followed by 30 cycles of 94° C., 30 s; 58° C. 30 s; 72° C. 4 min; and at 72° C. for 10 min. The LTR specific primers are used in the U5 region, which is conserved between all known PERV variants; primer LTR-5' (5'-GTGAACCCCAT-AAAAGCTGTC-3') (SEQ ID NO:20) is used to isolate 5'-flanking sequence, while primer LTR-3' (5'-GA-CAGCTTTTATGGGGTTCAC-3') (SEQ ID NO:21') is used to isolate 3'-flanking sequence.

Two PCR products are usually produced for each reaction, representing an LTR-internal proviral sequence, and an LTR-flanking DNA sequence. Both products are either direct sequenced or gel purified using the Qiaquick Gel Extraction kit (Qiagen), cloned into pCR2.1-TOPO (Invitrogen), and then sequenced.

Example 3

Screening for PERV Prevalence within Large White hDAF Pig Herd

The herd from which the test pigs are selected was a closed genetic herd. 30 animals were selected to exclude siblings and closely related animals and include as many ancestors (different parents and grandparents) as possible. This selection of animals on pedigree increases the number of variable genotypes tested compared to a random selection of animals as commonality by descent was minimized. DNA is isolated from pigs by either a standard proteinase K/phenol/chloroform method (Sambrook et al 1989), or using Qiagen Genomic tips (Qiagen) according to the manufacturers protocol. Based on sequence generated from the flanking PCR above, primer pairs are designed that would amplify between the PERV LTR, and the adjacent flanking DNA, yielding a PCR product that would uniquely identify each provirus. Primer specificity is confirmed using a positive control PCR with the lambda or cosmid clone the provirus is originally identified from. To score as positive, the PCR products derived from the pig genomic DNA have to be the same size as the positive control product. β-globin PCR is performed on each sample to confirm that the DNA is suitable for amplification, using ~35 ng template DNA in a 50 µl reaction containing: 150 nM each of primer β-globin F1 (5'-GCAGATTCCCAAACCTTCGCAGAG-3') (SEQ ID NO: 22) and β-globin R1(5'-TCTGCCCAAGTCCTAAATGTGCGT-3') (SEQ ID NO:23), 50 mM KCl, 10 mM Tris-HCl (pH 8.3), 1.5 mM MgCl$_2$, 200 nM each dNTP and 1.25 U Amplitaq Gold (PE Biosystems). Reactions are cycled as follows: 95° C. 9 min, 30 cycles of 95° C. 30 s, 58° C. 30 s, 72° C. 30 s, followed by 7 min at 72° C.

For the cosmid 78 provirus each reaction used ~60 ng template DNA in a 50µl reaction containing: 300 nM each of primer 78 ltrs (5'-GAA CCC CAT AAA AGC TGT CC-3') (SEQ ID No:24) and 78 ltras (5'-GAT CCT ATG TTG GGT GCATTT-3') (SEQ ID NO:25), 50 mM KCl, 10 mM Tris-HCl (pH 8.3), 1. 5 mM MgCl$_2$, 200 nM each dNTP, and 2 U Amplitaq Gold (PE Biosystems). Reactions are cycled as follows: 94° C. 9 min, followed by 35 cycles of 94° C. 30 s, 54° C. 30 s, 72° C. 30 s, and a final 10 min at 72° C. The predicted product size is 323 bp based on sequence analysis.

Reaction conditions for all remaining primer sets described below are as follows: ~20 ng template DNA in a 50 µl reaction containing 50 mM KCl, 10 mM Tris-HCl (pH 8.3), 1.5 mM MgCl$_2$, 150 nM each primer, 200 nM each dNTP and 1.25 U Amplitaq Gold (PE Biosystems).

Primer sets and cycle parameters used are as follows:

Provirus35 121 i: primers FLPR3 (5'-CATGACGGCAACTCCTGAAG-3') (SEQ ID NO:26) and revltr1 (5'-GTG AAC CCC ATA AAA GCT GTC-3') (SEQ ID NO:20) under the following cycle parameters: 95° C. 9 min, 35 cycles of 94° C. 1 min, 58° C. 1 min, 72° C. 2 min, followed by 10 min at 72° C. The predicted product size is 455 bp based on sequence analysis.

Provirus 21321: primers 21f2 (5'-GGTCTGTGACCTACTCCATA-3') (SEQ ID NO:29) and ltr1 (5'-GAC AGC TTT TAT GGG GTT CAC-3') (SEQ ID NO:21) under the following cycle parameters: 95° C 9 min, 35 cycles of 94° C. 1 min, 58° C. 1 min, 72° C. 2 min, followed by 10 min at 72° C. The predicted product size is 518 bp based on sequence analysis.

Provirus 73414i: primers 73-4r-3 (5'-GTCATGCCGTTCATTTGGGA-3') (SEQ ID NO:28) and revltr1 under the following cycle parameters: 95° C. 9 min, 40 cycles of 94° C. 1 min, 56° C. 1 min, 72° C. 2 min, followed by 10 mm at 72° C. The predicted product size is 388 bp based on sequence analysis.

Provirus 73414ii: primers73-3f-3 (5'-AGCAACAGAATTGAAGTCAG-3') (SEQ ID NO:29) and revltr1 under the same cycle parameters as72414i. The predicted product size is 438 bp based on sequence analysis.

Provirus 310518-5': the primers 31f8 (5'-GGATGGAGACTATGCTCAGC-3') (SEQ ID NO:30) and ltr1 under the following cycle parameters: 95° C. 9 min, 35 cycles of 94° C. 1 min, 56° C. 1 min, 72 C 2 min, followed by 10 min at 72° C. The predicted product size is 1641 bp based on sequence analysis.

Provirus 310518-3': the primers 31f2 (5'-AACTCATGATAAATGAAACACC-3') (SEQ ID NO:31) and revltr1 under the same cycle parameters as 310518-5'. The predicted product size is 815 bp based on sequence analysis.

Isolation of Proviruses Containing both Gag and Env Sequences

The cosmid library is screened for PERV A env and the lambda library for PERV B env and PERV gag as described above. Both libraries yield many more gag positive colonies than env positives, partly reflecting the non-PERV subtype selectivity of the gag probes, and in the case of the cosmid library the larger size of the gag probe used. 84 clones are identified from the cosmid library as being both gag and env A positive, of which 78 are recovered. Four of these 78 clones did not have inserts on sequence analysis, giving a total of 74 gag and env positive clones, which are purified to homogeneity through further rounds of screening. From the lambda library 40 plaques are initially isolated, of which 4 are not gag and env B positive on second round screening and are discarded. The remaining 36 positive plaques are purified to homogeneity. Multiple clones derived from each initial plaque are analysed to ensure that any instability of the insert would not affect the results.

The doubly positive cosmid clones are then analysed by restriction fragment digestion to identify duplicate clones by their identical restriction fragment patterns. 54 are unique by restriction fragment pattern analysis, 24 are duplicates of other clones. Only results for the unique clones are described below. As the yield of DNA from the lambda preparations is much lower than for the cosmid clones, lambda clones are also subjected to Southern blot analysis using gag and env probes as described, since the numbers are relatively small, all lambda cones are analysed further. Southern blotting shows that the majority of PERV b clones had a EcoRI RFLP with respect to the published PERV B sequence. Sequencing shows this to be a single silent base change in the gag gene, introducing a novel EcoRI site.

Each unique clone is then subjected to further analysis. Where there are two or more cosmid clones with identical RFLP patterns, then two or more representatives of each are analyzed to confirm results. The result of the PCR is regarded as positive if the clone gave a PCR product approximately the size expected for the intact ORF based on published PERV sequences.

The gag PCR shows major differences between the PERV A screened cosmid library, and the PERV B screened lambda library. Whilst 32/34 lambda clones gave gag PCR products, only 13/54 cosmid clones gave gag PCR products. Sequencing from the cosmid MCS shows that this was caused by cloning deletions in the env gene in some cases. However for the majority of clones that give no gag PCR product, sequence adjacent to the MCS is not PERV sequence, indicating that no cloning deletion had occurred. No smaller than predicted gag products, representing proviruses with internal deletions, are detected from either library. Protein truncation testing of apparently full length gag genes for cosmid clones showed that 8/13 clones have intact gag open reading frames, 1/15 have a truncated ORF, while 4/13 clones are not tested as they had already been excluded from analysis on the basis of a truncated env gene. In contrast, only 11/32 lambda clones have an intact gag ORF, 20/34 have a truncated gag ORF. 1/32 is not analysed by PTT as it has previously been found to be defective.

The pol PCR primers are designed to amplify a ~2.7 kb product, based on sequence alignments with the prototype PERV sequence AF038600. 16/54 cosmid clones give pol PCR products. A smaller ~720 bp product is amplified from some cosmids, which is the sole product from cosmid 5. Sequencing of this product shows >96% homology over three regions to the PERV pol gene of AF038600 (a PERV C clone) with two internal deletions. There is homology from the pot start ATG codon at base 2307 of AF038600 to base 2496, then a deletion, and homology from bases 3721-4051, then a deletion, and homology from base 4872 to the end of the PCR product at base 5070, giving a sequenced product size of 718 bp. This small product does not encode a functional pol protein, and clones giving such PCR products are regarded as defective. Some clones also give a larger than predicted 3.8 k b product. The 3.8 kb product could potentially encode a functional pol protein, but this is not investigated further as work on gag and env showed clones giving this product as defective in at least one other gene. As shown, a few cosmids give both the predicted full length product, and the 718 bp deleted product. In these cases the larger fragment is assumed to be associated with the provirus under study, rather than another provirus on the cosmid clone, due to the possibility that on the ~40 kb cosmid inserts that there are two or more proviruses, or proviral fragments. Of 18 lambda clone subjected to pol PCR, only one did not give the expected 2.7 kb product. The remainder of clones had previously been identified as being defective in gag or env, and were not tested. Attempts to use protein truncation testing to look for ORFs in these the larger products failed to yield translation products under a range of conditions using both rabbit reticulocyte lysate or wheatgerm lysate. Thus PTT is not performed on pol genes.

For the env PCR, 18/54 cosmid clones give a PCR product of the predicted size of the ORF at ~2 kb, 35/54 gave no PCR product, and one was not tested. From the lambda library 31/34 give full length products and 3/34 no product. No smaller products representing env internal deletions are identified. PTT is performed on the PCR products. Only 2/18 cosmid clones give translation products, which is confirmed by carboxy terminal epitope tagging PTT as described. 16/18 give truncated and non functional env translation products. Sequence analysis of the sole clone that also give a full-length gag product revealed that this is in fact a PERV b clone. Sequence analysis of a number of other clones show that they were PERV A as expected. In contrast 13/31 of the PERV B clones give full-length env translation products on PTT, 10/31 give truncated products, while 8 are not analysed, as they have already been observed to be gag defective.

Where the clones are amplifiable by one or more sets of primers, but give no product for one or more of the other ORFs, it is presumed that the remaining proviral sequences are defective, and analysis is not continued further. By these criteria, no intact PERV a clones are identified from the cosmid library: of the 54 unique clones, only one give full-length PTT products for gag and env, together with an appropriate sized pol PCR product. Sequence analysis of this clone, cosmid 78, show that it is PERV B. From the lambda library six PERV B clones are identified as being potentially full length, clones 21321, 2441, 35121, 310518, 65321 and 73414. Analysis of these seven clones is continued further as described below.

A number of gag and env positive cosmid clones isolated do not amplify with the gag, pol or env primer sets. To exclude the possibility that these represented major sequence variants on the published PERV proviruses, and hence are not amplified by the PCR primers used, these are further analysed in two ways. Sequenced from the cloning sites into the insert, to detect if the provirus have been truncated during the cloning process. Additionally, Southern blots of SmaI digested cosmid DNA are probed with biotin labelled oligonucleotides homologous to the region around the primer binding site (PBS) and env LTR junction. It is assumed that, due to the sequence conservation seen about these regions in all known PERV variants, that failure to bind these oligos would indicate a grossly deleted provirus. Most of these clones show no signal from either of these probes, indicating that they are deleted at both ends. The remainder are deleted either at one end or the other. Cosmid clone 74 shows signals for both primer binding site and env-LTR.

Analysis of Flanking Sequence and Proviral Prevalence

Sequence data is obtained for the LTR-flanking DNA junction for each unique clone intact clone above using the linker-mediated PCR method described above. For most clones 3'-flank sequence is obtained (cosmid 78 and lambda clones 65321, 2441, 73414 and 35121), for lambda done 21321 5'-flank sequence is obtained, and for 310518 both 3' and 5'-flanking sequence is obtained.

Lambda clones 65321, 2441 and 310518 give a common flanking sequence, confirming that they represented a single provirus. Lambda clones 73414 and 35121 both give two different LTR-3'-flank sequences (termed 73414i and 73414ii, 35121i and 35121ii), 73414ii and 35121ii are identical, while the other sequences showed no similarity, indicating that the lambda clones are contiguous, containing 3 tandemly arranged proviruses/proviral remnants. The 3'-flank sequence of cosmid 78 is not the same as any of these.

From the 5'-flank sequence obtained, clones 21321 and 310518 are different, but as 5'-flank sequence is not obtained for the other clones, it is not possible to determine if 21321 was the same provirus as the 73414/35121 group, or cosmid 78. However, although the pattern of prevalence in pigs obtained below are identical for 35121 and 21321, there are a number of nucleotide and amino acid differences in Env that confirm that they represent different proviruses.

Primer pairs are designed for each of these unique LTR-flanking DNA junction sequences to analyse 30 unrelated pigs for the presence of each of the proviruses. Suitability of the DNA for PCR amplification is confirmed using porcine β-globin primers, where all samples gave broadly equivalent product yields. The PERV-Cosmid 78 provirus is present in 6/30 pigs, 24/30 pigs were negative for this provirus. 3/30 pigs (G579, H744, H440) are strongly positive, while 3/30 give a lower product yield (H522, G768, H338). Provirus 734141 is present in 3/30 pigs, while provirus 73414ii is in 30/30 pigs. Provirus 35121i is present in 24/30 pigs. A smaller ~200 bp fragment is produced from lambda clone 35121, the positive control, which is also visible in some of the pig PCR reactions. As this did not interfere with the assay it is disregarded, and is not sequenced to determine its origin. For provirus 310518 independent PCRs are performed for the 5'- and 3'-flanks. These give concordant results in 29/30 pigs, 23/30 pigs are positive for the provirus and 6/30 negative. Pig H539 is positive for the 3'-LTR-flank junction and negative for the 5'-LTR-flank junction, thus giving an ambiguous result. Provirus 21321 is present in 24/30 pigs.

Sequence Analysis and Transfection Analysis

Env

Sequencing of env genes of all proviruses confirmed the presence of a full length Env ORF, confirming the PTT results. Comparison of the proviral env with published PERV sequences show a high degree of homology (>99%) with the published PERV B sequence Y12239 at both the nucleotide and amino acid levels. The single sequence labelled 2441 is the concensus sequence obtained from clones 65321, 2441 and 310518 env sequences. Sequencing of env from lambda clones 73414 and 310518 give only a single env concensus sequence each, despite the two different 3'-LTRs that are present in these clones.

The receptor interacting VRA and VRB regions in the middle of the protein shows no variation from the prototype sequence, although there are a few polymorphisms between the env genes that confirmed that they represent different proviruses.

All clones are intact in all three open reading frames, as confirmed by PTT and sequencing. Sequence analysis of homologies with published PERV variants showed expectedly high levels of homology between them.

Summary of Cosmid Clones

All results on cosmid clones positive for gag and env are tabulated below. Clones were numbered sequentially on initial picking. Clones shown below are unique as indicated by a "U" in the RFLP pattern column. Where duplicate clones were identified, the number of such duplicates is noted in this column. Clone numbers not in the table were either not recovered from the first round screening, or were duplicates of other clones. PCR results are reported as +, when a product of the correct size was obtained, and − when no product was obtained. CD indicates that on sequencing from the vector arms, that gag sequence was adjacent to vector sequence as a result of cloning deletions, such clones are recorded as defective only if negative results were obtained for the env gene. In the case of clone 56 the clone was truncated, but negative PCR results were obtained for pol and env, this is recorded as a cloning deletion as was not analysed further. Additionally for pol, a + alone means that a product of the predicted size was obtained, a + with an l or s means a respectively larger or smaller product was observed, in the absence of the predicted product. For the PTT results, FL means that a full length protein was translated, TP means that a truncated protein was produced, relative to a control. For the env HA PTT a + means a signal was seen, (confirmatory of a full length protein), a − means no signal was seen (confirmatory of a truncated protein).

In the 'defective?' column defective clones are indicated by 'yes' followed by the reason they are defective. Where products were obtained for either gag, pot or env, the clone is described as being defective in either genes yielding truncated PTT products, or genes failing to give PCR products. Where no products were observed for gag, pol or env, results from the Southern blots using PBS or env-LTR probes were used to confirm that the clones were defective.

| clone | RFLP pattern | Gag PCR | Gag PTT | Pol PCR | Env PCR | Env PTT | Env HA PTT | Defective? |
|---|---|---|---|---|---|---|---|---|
| 1 | +1 | CD | | +l | + | TP | − | Yes, env |
| 3 | U | − | | − | − | | | Yes |
| 4 | U | + | FL | + | − | | | Yes env |
| 5 | U | − | | +s | − | | | Yes, gag pol and env |
| 6 | U | − | | + | + | TP | | Yes, env |
| 7 | +11 | − | | + | + | TP | | Yes, gag and env |
| 9 | U | − | | + | + | TP | | Yes, gag and env |
| 10 | U | − | | +l | − | | | Yes, gag and env |
| 12 | U | − | | − | − | | | Yes |
| 13 | +6 | − | | +l | − | | | Yes, gag and env |
| 15 | U | − | | + | + | TP | | Yes, gag and env |
| 18 | U | + | ND | + | + | TP | | Yes, env |
| 19 | U | − | | − | − | | | Yes |
| 21 | U | + | ND | − | − | | | Yes, pol and env |
| 22 | U | − | | − | − | | | Yes |
| 24 | U | CD | | +l | − | | | Yes env |
| 25 | U | + | | + | + | TP | | Yes env |
| 27 | U | − | | + | − | | | Yes, gag and env |
| 29 | U | − | | +l | − | | | Yes, gag and env |
| 30 | U | − | | − | − | | | Yes, gag and env |
| 31 | U | − | | +l | − | | | Yes, gag and env |
| 34 | U | − | | +l | − | | | Yes, gag and env |
| 35 | U | − | | + | + | TP | | Yes, gag and env |
| 36 | U | CD | | ND | ND | | | Cloning deletion |
| 38 | U | − | | − | − | | | Yes, gag and env |
| 39 | U | − | | − | − | | | Yes, gag and env |
| 41 | U | − | | − | − | | | Yes, gag and env |
| 43 | U | − | | − | − | | | Yes, gross deletion |
| 45 | U | − | | +l | − | | | Yes, gag and env |
| 46 | U | + | TP | + | + | FL | + | Yes, gag |
| 47 | U | − | | − | − | | | No insert |
| 48 | U | + | FL | + | + | TP | − | Yes, env |
| 49 | U | + | FL | + | + | TP | − | Yes, env |
| 53 | U | − | | − | − | | | Yes, gag and env |
| 54 | +1 | − | | + | + | TP | | Yes, gag and env |
| 56 | U | CD | | − | − | | | Cloning deletion |
| 57 | U | − | | + | + | TP | | Yes, env |
| 58 | U | + | FL | + | + | TP | − | Yes, env |
| 59 | U | + | ND | +l | − | | | Yes, env |
| 60 | U | + | FL | + | + | TP | − | Yes, env |
| 61 | U | + | FL | + | + | TP | − | Yes, env |
| 62 | U | − | | | | | | Yes, env |
| 64 | U | CD | | +l | − | | | Yes, env |
| 66 | U | − | | +l | − | | | Yes, gag and env |
| 67 | U | CD | | +l | − | | | Yes, env |
| 69 | U | − | | + | − | | | Yes, gag and env |
| 70 | U | − | | − | − | | | Yes, gag and env |
| 74 | U | − | | +l | − | | | Yes |
| 77 | U | − | | +l | − | | | Yes gag and env |
| 78 | U | + | FL | + | + | FL | + | No-INTACT |
| 79 | +1 | − | | − | − | | | Yes, gag and env |
| 82 | U | − | | + | − | | | Yes, gag and env |
| 83 | U | + | FL | + | + | TP | − | Yes, env |
| 84 | U | − | | + | − | | | Yes, gag and env |

Summary of Analysis of Gag and Env Double Positive Clones Obtained from a PERV B Screened Large White Pig Lambda Library The columns and abbreviations are the same as in the table above, with the exception of the Southern blot data column. PERV B indicates that the restriction pattern obtained was identical to the published PERV B provirus Y17013, while PERV B Var indicates that there was a variant RFLP pattern observed indicating that the proviral sequence was either variant from the published data or was deleted somewhere in the proviral sequence. From each original plaque picked multiple plaques were analysed, the clone ID shown is the number of the clone that was analysed in greatest detail, and was the least defective.

| clone | PBS band sizes (kb) | env band sizes | comments |
|---|---|---|---|
| 12 | 0.5, 0.65 | – | No env signal: defective |
| 13 | – | – | No signal for PBS-gag or env-LTR: defective |
| 19 | 1.2, 2.5 | 1.2 | Env and PBS signal on the same fragment, therefore deleted |
| 30 | – | – | No signal for PBS-gag or env-LTR: defective |
| 43 | 2.3 | + | Env and PBS signal on the same fragment, therefore deleted |
| 53 | – | – | No signal for PBS-gag or env-LTR: defective |

| Original Plaque ID | Clone ID | Southern Blot data | Gag PCR | Gag PTT | Pol PCR | Env PCR | Env PTT | Defective |
|---|---|---|---|---|---|---|---|---|
| 2.1 | 21321 | PERV B Var | + | FL | + | + | FL | No-INTACT |
| 2.2. | 22332 | ND | + | TP | ND | + | FL | Yes gag |
| 2.4 | 2441 | PERV B Var | + | FL | + | + | FL | No-INTACT |
| 2.5 | 25321 | PERV B Var | + | TP | + | + | TP | Yes gag and env |
| 2.6 | 2622 | PERV B Var | + | TP | ND | + | ND | Yes gag |
| 2.7 | 27244 | PERV B Var | + | TP | + | + | FL | Yes gag |
| 2.8 | 28321 | PERV B Var | + | TP | ND | + | ND | Yes gag |
| 3.1 | 31211 | PERV B Var | + | TP | + | + | FL | Yes gag |
| 3.2 | 3211 | PERV B Var | + | TP | + | + | TP | Yes gag and env |
| 3.3 | 3321 | PERV B | + | TP | ND | + | FL | Yes gag |
| 3.4 | 34321 | PERV B Var | + | TP | ND | + | FL | Yes gag |
| 3.5 | 35121 | PERV B | + | FL | + | + | FL | No-INTACT |
| 3.6 | 3611 | PERV B Var | + | TP | ND | + | ND | Yes gag |
| 3.7 | 3711 | PERV B | – | – | – | – | | Yes |
| 3.8 | 3821 | PERV B | + | TP | ND | + | ND | Yes gag |
| 3.9 | 39111 | PERV B | + | FL | ND | + | TP | Yes env |
| 3.10 | 310518 | PERV B | + | FL | + | + | FL | No-INTACT |
| 3.12 | 312146 | PERV B Var | + | TP | ND | + | ND | Yes gag |
| 4.1 | 411 | PERV B Var | + | TP | ND | + | ND | Yes gag |
| 4.3 | 436 | PERV B Var | + | ND | + | – | | Yes env |
| 4.4 | 441** | PERV B Var | + | FL* | ND | + | FL* | See legend |
| 4.5 | 45411 | PERV B | + | FL | + | + | TP | Yes env |
| 5.1 | 5112 | PERV B Var | + | FL | + | + | TP | Yes env |
| 5.2 | 52111 | PERV B | + | TP | ND | + | TP | Yes gag and env |
| 6.1 | 61121 | PERV B Var | + | TP | ND | + | ND | Yes, gag |
| 6.2 | 62321 | PERV B | + | TP | + | + | FL | Yes gag |
| 6.4 | 6411 | PERV B | + | TP | ND | + | ND | Yes gag |
| 6.5 | 65321 | PERV B Var | + | FL | + | + | FL | No-INTACT |
| 7.3 | 73414 | PERV B Var | + | FL | + | + | FL | No-INTACT |
| 7.4 | 74411 | PERV B Var | + | FL | + | + | TP | Yes env |
| 7.5 | 75321 | PERV B Var | – | | ND | – | | Yes gag and env |
| 8.1 | 81111 | PERV B Var | + | TP | + | + | TP | Yes gag and env |
| 8.2 | 82222 | PERV B Var | + | TP | + | + | TP | Yes gag and env |
| 8.3 | 8311 | PERV B Var | + | TP | ND | + | TP | Yes gag and env |

Analysis of cosmid clones which were gag and env positive, and gave no PCR product for gag, pol or env.

Cosmid DNA was digested with SmaI, electrophoresed, and subjected to Southern blotting. Blots were probed with a biotin labelled probe against either PBS-gag or env-LTR, followed by detection of probe with steptavidin-HRP conjugate and ECL detection as described. <6.0 kb means that the product was larger than the biggest marker used, hence size could not be determined accurately.

-continued

| clone | PBS band sizes (kb) | env band sizes | comments |
|---|---|---|---|
| 59 | >6.0 | – | No env signal: defective |
| 62 | >6.0 | – | No env signal: defective |
| 66 | >6.0 | – | No env signal: defective |
| 69 | – | – | No signal for PBS-gag or env-LTR: defective |
| 70 | – | – | No signal for PBS-gag or env-LTR: defective |

-continued

| clone | PBS band sizes (kb) | env band sizes | comments |
|---|---|---|---|
| 84 | 1.3 | + | Env and PBS signal on the same fragment, therefore deleted |

Flanking sequence are obtained for all clones by the linker-mediated PCR method described. For most clones 3'-flank sequence are obtained (cosmid 78 and lambda clones 65321, 2441, 73414 and 35121), for lambda clone 21321 5'-flank sequence are obtained, and for 310518 both 3' and 5'-flanking sequence are obtained.

Lambda clones 65321, 2441 and 310518 give a common flanking sequence, confirming that they represented a single provirus. Lambda clones 73414 and 35121 both give two different LTR-3'-flank sequences (termed 73414i and 73414ii, 35121i and 35121ii), 73414ii and 35121ii are identical, while the other sequences showed no similarity, indicating that the lambda clones are contiguous, containing 3 tandemly arranged proviruses/proviral remnants. The 3'-flank sequence of cosmid 78 is not the same as any of these.

From the 5'-flank sequence obtained, clones 21321 and 310518 are different. Differences in env sequences confirm that provirus 21321 is distinct from the other clones.

Sequence Alignment of Translated Env Genes for Five Intact Proviruses.

Env genes were sequenced as described, and translated. Sequence alignments were performed

```
12239   LTWLIIDPDTGVTVNSTRGVAPRGTWWPELHFCLRLINPAVKSTPPNLVRSYGFYCCPGT c78     LTWLIIDPDTGVTVNSTRGVAPRGTWWPELHFCLRLINPAVKSTPPNLVRSYGFYCCPGT

2441    LTWLIIDPDTGVTVNSTRGVAPRGTWWPELHFCLRLINPAVKSTPPNLVRSYGFYCCPGT

73414   LTWLIIDPDTGVTVNSTRGVAPRGTWWPELHFCLRLINPAVKSTPPNLVRSYGFYCCPGT

35121   LTWLIIDPDTGVTVNSTRGVAPRGTWWPELHFCLRLINPAVKSTPPNLVRSYGFYCCPGT

21321   LTWLIIDPDTGVTVNSTRGVAPRGTWWPELHFCLRLINPAVKSTPPNLVRSYGFYCCPGT
        ************************************************************

Y12239  EKEKYCGGSGESFCRRWSCVTSNDGDWKWPISLQDRVKFSFVNSGPGKYKVMKLYKDKSC c78     EKEKYCGGSGESFCRRWSCVTSNDGDWKWPISLQDRVKFSFVNSGPGKYKVMKLYKDKSC

2441    EKEKYCGGSGESFCRRWSCVTSNDGDWKWPISLQDRVKFSFVNSGPGKYKVMKLYKDKSC

73414   EKEKYCGGSGESFCRRWSCVTSNDGDWKWPISLQDRVKFSFVNSGPGKYKVMKLYKDKSC

35121   EKEKYCGGSGESFCRRWSCVTSNDGDWKWPIFLQDRVKFSFVNSGPGKYKVMKLYKDKSC

21321   EKEKYCGGSGESFCRRWSCVTSNDGDWKWPISLQDRVKFSFVNSGPGKYKVMKLYKDMSC
        ******************************  *** ******************** **

Y12239  SPSDLDYLKISFTEKGKQENIQKWINGMSWGIVFYKYGGGAGSTLTIRLRIETGTEPPVA c78     SPSDLDYLKISFTEKGKQENIQKWINGMSWGIVFYKYGGGAGSTLTIRLRIETGTEPPVA

2441    SPSDLDYLKISFTEKGKQENIQKWINGMSWGIVFYKYGGGAGSTLTIRLRIETGTEPPVA

73414   SPSDLDYLKISFTEKGKQENIQKWINGMSWGIVFYKYGGGAGSTLTIRLRIETGTEPPVA

35121   SPSDLDYLKISFTEKGKQENIQKWINGMSWGIVFYKYGGGAGSTLTIRLRIETGTEPPVA

21321   SPSDLDYLKISFTEKGKQENIQKWINGMSWGIVFYKYGGGAGSTLTIRLRIETGTEPPLA
        *********************************************************:*

Y12239  VGPDKVLAEQGPPALEPPHNLPVPQLTSLRPDITQPPSNGTTGLIPTNTPRNSPGVPVKT c7S     VGPDKVLAEQGPPALEPPHNLPVPQLTSLRPDITQPPSNGTTGLIPTNTPRNSPGVPVKT

2441    VGPDKVLAEQGPPALEPPHNLPVPQLTSLRPDITQPPSNGTTGLIPTNTPRNSPGVPVKT

73414   VGPDKVLAEQGPPALEPPHNLPVPQLTSLRPDITQPSSNGTTGLIPTNTPRNSPGVPVKT

35121   VGPDKVLAEQGPPALEPPHNLPVPQLTSLRPDITQPPSNGTTGLIPTNMPRNSPGVPVKT

21321   VGPDKVLAEQGPPALEPPHNLPVPQLTSLRPDITQTPSNGTTGLIPTNTPRNSPGVPVKT
        ***********************************  ********** ***********

Y12239  GQRLFSLIQGAFQAINSTDPDATSSCWLCLSSGPPYYEGMAKEGKFNVTKEHRNQCTWGS c78     GQRLFSLIQGAFQAINSTDPDATSSCWLCLSSGPPYYEGMAKEGKFNVTKEHRNQCTWGS
```

-continued

```
2441    GQRLFSLIQGAFQAINSTDPDATSSCWLCLSSGPPYYEGMAKEGKFNVTKERRNQCTWGS

73414   GQRLFSLIQGAFQAINSTDPDATSSCWLCLSSGPPYYEGMAKEGKFNVTKERRNQCTWGS

35121   GQRLFSLIQGAFQAINSTDPDATSSCWLCLSSGPPYYEGMAKEGKFNVTKEHRNQCTWGS

21321   GQRLFSLIQGAFQAINSTDPDATSSCWLCLSSGPPYYEGMAKEGKFNVTKEHRNQCTWGS
        ****************************************************:********

Y12239  RNKLTLTEVSGKGTCIGKAPPSHQHLCYSTVVYEQASENQYLVPGYNRWWACNTGLTPCV c78     RNKLTLTEVSGKGTCIGKAPPSHQHLCYSTVVYEQASENQYLVPGYNRWWACNTGLTPCV

2441    RNKLTLTEVSGKGTCIGKAPPSHQHLCYSTVVYEQASENQYLVPGYNRWWACNTGLTPCV

73414   RNKLTLTEVSGKGTCIGKAPPSHQHLCYSTVVYEQASENQYLVPGYNRWWACNTGLTPCV

35121   RNKLTLTEVSGKGTCIGKAPPSHQHLCYSTVVYEQASENQYLVPGYNRWWACNTGLTPCV

21321   RNKLTLTEVSGKGTCIGKAPPSHQHLCYSTVVYEQASENQYLVPGYNRWWACNTGLTPCV
        ***********************************************************

Y12239  STSVFNQSKDFCVMVQIVPRVYYHPEEVVLDEYDYRYNRPKREPVSLTLAVMLGLGTAVG c78     STSVFNQSKDFCVMVQIVPRVYYHPEEVVLDEYDYRYNRPKREPVSLTLAVMLGLGTAVG

2441    STSVFNQSKDFCVMVQIVPRVYYHPEEVVLDEYDYRYNRPKREPVSLTLAVMLGLGTAVG

73414   STSVFNQSKDFCVMVQIVPRVYYHPEEVVLDEYDYRYNRPKREPVSLTLAVMLGLGTAVG

35121   STSVFNQSKDFCVMVQIVPRVYYHPEEVVLDEYDYRYNRPKREPVSLTLAVMLGLGTAVG

21321   STSVFNQSKDFCVMVQIVPRVYYHPEEVVLDEYDYRYNRPKREPVSLTLAVMLGLGTAVG
        ***********************************************************

Y12239  VGTGTAALITGPQQLEKGLGELHAAMTEDLRALEESVSNLEESLTSLSEVVLQNRRGLDL c78     VGTGTTALTTGPQQLEKGLGELHAANTEDLRALEESVSNLEESLTSLSEVVLQNRRGLDL

2441    VGTGTAALITGPQQLEKGLGELHAAMTEDLRALEESVSNLEESLTSLSEVVLQNRRGLDL

73414   IGTGTAALITGPQQLEKGLGELHAAMTEDLRALEESVSNLEESLTSLSEVVLQNRRGLDL

35121   VGTGTAALITGPQQLEKGLGELHAANTEDLRALEESVSNLEESLTSLSEVVLQNRRGLDL

21321   VGTGTAALITGPQQLEKGLGELHAAMTEDLRALEESVSNLEESLTSLSEVVLQNRRGLDL
        :****:******************************************************

Y12239  LFLREGGLCAALKEECCFYVDHSGAIRDSMSKLRERLERRRREREADQGWFEGWFNRSPW (SEQ ID NO: 32)

c78     LFLREGGLCAALKEECCFYVDHSGAIRDSMSKLRERLERRRREREADQGWFEGWFNRSPW (SEQ ID NO: 33)

2441    LFLREGGLCAALKEECCFYVDHSGAIRDSMSKLRERLERRRREREADQGWFEGWFNRSPW (SEQ ID NO: 34)

73414   LFLREGGLCAALKEECCFYVDHSGAIRDSMSKLRERLERRRREREADQGWFEGWFNRSPW (SEQ ID NO: 35)

35121   LFLREGGLCAALKEECCFYVDHSGAIRDSMSKLRERLERRRREREADQGWFEGWFNRSPW (SEQ ID NO: 36)

21321   LFLREGGLCAALKEECCFYVDHSGAIRDSMSKLRERLERRRREREADQGWFEGWFNRSPW (SEQ ID NO: 37)
        ***********************************************************
```

Example 4

Gene Targeting in PERV

The first step in the targeting strategy begins by generating a targeting vector, containing the desired gene mutation and selected polynucleotide flanking sequences. This is introduced into embryonic stem cells by electroporation. In most cells the targeting vector inserts randomly into the target cell genome. However, in a few cells homologous DNA sequences in the targeting vector pair with homologous sequences in the target cells chromosomal DNA and recombine, introducing the mutation to the genome. If such gene manipulation is designed to prevent expression of the targeted gene it is called a null mutation or complete knockout. Other modifications, such as point mutations or deletions can be introduced to study different domains and subdomains of the gene product in situ.

Preferably, a minimal targeting arm length on one side of 1 kb, with at least 2-3 kb on the other side is used. There is no reason why the two targeting arms can't be of approximately the same length. More ~2 kb in size. There may be a significant advantage in using substantially longer targeting arms; however, large constructs are more difficult to manipulate. Targeting arms of ~2 kb on each side will yield homologous recombination efficiencies of 1-2%, which are adequate for most purposes.

It is feasible to PCR the targeting arms using genomic DNA derived from source animal, or from cloned genomic DNA. A few PCR errors seem to cause few (if any) problems for efficient homologous recombination. PCR certainly makes the ends of fragments easier to manipulate for insertion into vectors containing Neo.

Two selectable markers are commonly introduced into the targeting vector to allow identification of embryonic stem cell clones that have undergone successful homologous recombination. A positive selectable marker promotes survival of cells that have integrated the targeting vector either by homologous or non-homologous recombination. A negative selectable marker is used to enrich cells that have integrated the targeting vector by homologous recombination and to eliminate those that have incorporated the targeting vector in a non-homologous manner. The positive selectable marker, typically a neomycin-resistance gene, is flanked by the DNA sequence of the gene to be targeted. The negative selection marker, usually a thymidine kinase gene cassette, is cloned at the end of the targeting vector. When homologous recombination occurs, regions containing the targeting gene sequence, together with the neomycin cassette, replace the corresponding nucleotide sequence in the chromosome. Since the thymidine kinase gene resides outside of the region of homology, it does not integrate into the chromosome and is ultimately degraded. However, if the targeting vector sequence is integrated non-specifically into the chromosome by non-homologous recombination, the whole vector, including the thymidine kinase gene, can be inserted.

Treating targeted cells with neomycin kills those that have failed to integrate the targeting vector, and treatment with gancyclovir kills those that have retained the thymidine kinase gene. In this way, it is possible to select cells bearing targeting sequences inserted into the chromosome by homologous recombination. The proper integration of targeting sequences is confirmed by polymerase chain reaction (PCR) or by genomic Southern blotting. For gene targeting, the selected embryonic stem cells are expanded and injected into the blastocyst cavity of a pre-implantation embryo and the blastocyst is then transferred into the uterus of a pseudo-pregnant mother. The resulting animal is a chimera, consisting of cells derived from the targeted donor embryonic stem cells and host blastocyst.

For gene targeting in pigs, effective manipulation of porcine embryonic stem cells and blastocyst injection to produce chimeric offspring is difficult. Nuclear transfer represents a preferred method for generating gene-targeted pigs, for e.g. PERV-negative pigs. Since a nuclear transfer pig is derived wholly from a single genetically modified cell, the resulting pig is will carry this genetic modification in all cells including the germ cells and therefore will not be chimeric.

Most targeting constructs in the past have used both Neo and HSV-TK to perform +/- selection. However, gancyclovir treatment of ES cells is quite toxic, and in the case of ES cells, it can negatively affect the ability of ES cells to go germline. Hence a lower rate of homologous recombination is often exchanged for a better rate of germline transmission. Several different kinds of Neo cassettes are available. Neo that is flanked by Lox-P sites (see below), so that the PGK-Neo selectable marker cassette can be removed by CRE-recombinase to avoid potential problems with "neighborhood effects" of the PGK-Neo cassette is preferred. Recent work has suggested that this neighborhood effect is very problematic in multigene clusters (Pham et al, PNAS 93: 13090, 1996; Hug et al, MCB 16: 2906, 1996). If it is known that ones target gene is in a multigene cluster, one will need to anticipate the potential neighborhood effects of retained Neo cassettes Detection of Homologous Recombination Events Although PCR can be used to detect homologous recombinants, it is not recommended. It is preferred to develop a unique probe that is external to the targeting sequences themselves and use it to screen using Southern analysis. It does not matter whether this probe is upstream or downstream from the targeting construct, it only matters that it is completely external, and that it contains no repetitive DNA elements. This probe should be used in conjunction with Southern analysis of each cell clone to determine whether or not a targeting event has occurred. In addition to defining a homologous recombination band, Southern analysis also allows one to assess the molarity of mutant bands, which is difficult to do by PCR. Basically, if the wild-type and mutant bands are not equal in intensity, one should be suspicious that the targeted clone is contaminated with wild-type cells. If the targeted bands look correct on the Southern, but the molarity is suspect, then it is strongly recommended that the cells be re-selected in G418, or even replated by limiting dilution to subclone the cells of interest.

The diagram below shows examples of PERV gene-targeting constructs comprising either 3' or 5' unique PERV flanking DNA sequence in one vector arm and non-unique PERV genomic sequence comprising the other vector arm. In these constructs, the env gene is arbitrarily disrupted in the 5'-specific construct and the gag gene in the 3'-specific one. This however is not a design constraint, and thus any region of the PERV genome may be disrupted or deleted with a suitable targeting construct.

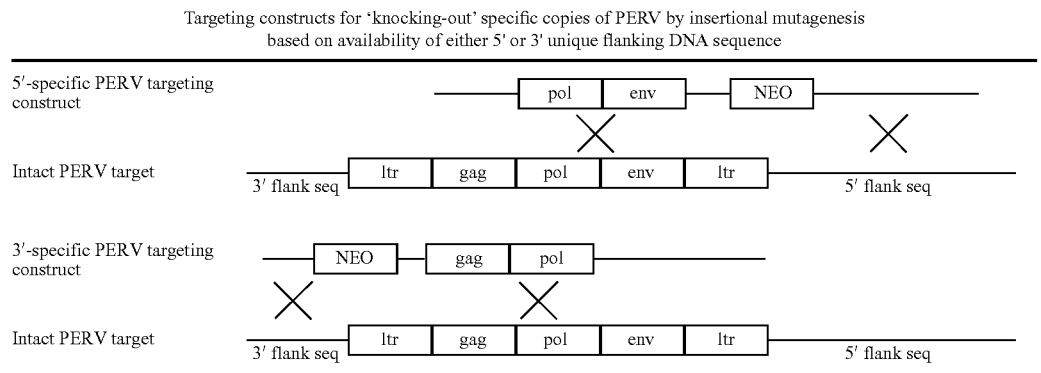

Targeting constructs for 'knocking-out' specific copies of PERV by insertional mutagenesis based on availability of either 5' or 3' unique flanking DNA sequence

The invention claimed is:

1. An isolated polynucleotide comprising a sequence selected from the group consisting of: SEQ ID. No. 1, SEQ ID. No. 2, and fragments thereof comprising more than 500 contiguous nucleotides of SEQ ID No. 1, or SEQ ID. No. 2.

2. An isolated polynucleotide comprising a sequence at least 95% identical to a sequence selected from the group consisting of: SEQ ID. No. 1, SEQ ID No. 2, and fragments thereof comprising more than 500 contiguous nucleotides of SEQ ID No. 1 or SEQ ID. No. 2.

3. A vector comprising at least one isolated polynucleotide according to claim 2.

4. A method of screening a pig for the presence of a porcine endogenous retrovirus said method comprising:
   (i) providing a sample comprising nucleic acids from the pig;
   (ii) contacting the sample with a polynucleotide for detecting a porcine endogenous retrovirus in the sample, wherein the polynucleotide comprises a fragment of a sequence at least 95% identical to a sequence selected from the group consisting of: SEQ ID No. 1 and SEQ ID No. 2, which fragment is at least 500 nucleotides in length; and
   (iii) identifying whether the pig has the porcine endogenous retrovirus, thereby screening the pig for the presence of a porcine endogenous retrovirus.

5. A detection kit for the detection of a porcine endogenous retrovirus, the kit comprising:
   (i) a polynucleotide for detection of a porcine endogenous retrovirus, wherein the polynucleotide is a polynucleotide according to claim 2.

6. The polynucleotide of claim 2, wherein the polynucleotide comprises a sequence at least 95% identical to a sequence selected from the group consisting of: SEQ ID. No. 1, and SEQ ID No. 2.

7. The method of claim 4, wherein the fragment comprises up to 2000 nucleotides.

8. The method of claim 4, wherein the sample comprising nucleic acids from the pig comprises a genomic DNA library.

9. The method of claim 4, wherein the method comprises amplifying the nucleic acids in the sample by polymerase chain reaction (PCR).

* * * * *